United States Patent
Irizarry et al.

(10) Patent No.: US 12,017,911 B2
(45) Date of Patent: Jun. 25, 2024

(54) DRY FOG PRODUCTION AND APPLICATION METHODS AND SYSTEMS

(71) Applicant: Bio Domain Systems Corporation, Raleigh, NC (US)

(72) Inventors: Harold Irizarry, Indiatlantic, FL (US); Brian Conner, Guntersville, AL (US); Michael Conner, Guntersville, AL (US); Robert Bell, Guntersville, AL (US)

(73) Assignee: Bio Domain Systems Corporation, Raleigh, NC (US)

(*) Notice: Subject to any disclaimer, the term of this patent is extended or adjusted under 35 U.S.C. 154(b) by 737 days.

(21) Appl. No.: 17/203,923

(22) Filed: Mar. 17, 2021

(65) Prior Publication Data
US 2021/0261410 A1     Aug. 26, 2021

Related U.S. Application Data

(63) Continuation of application No. PCT/US2019/051612, filed on Sep. 17, 2019.

(60) Provisional application No. 62/732,513, filed on Sep. 17, 2018, provisional application No. 62/732,512, filed on Sep. 17, 2018.

(51) Int. Cl.
| | | |
|---|---|---|
| C01B 11/08 | (2006.01) | |
| A61L 2/22 | (2006.01) | |
| A61L 9/14 | (2006.01) | |
| A61L 101/06 | (2006.01) | |

(52) U.S. Cl.
CPC ............. *C01B 11/08* (2013.01); *A61L 2/22* (2013.01); *A61L 9/14* (2013.01); *A61L 2101/06* (2020.08); *A61L 2202/11* (2013.01); *A61L 2202/17* (2013.01)

(58) Field of Classification Search
CPC ..... A61L 2/22; A61L 2/24; A61L 9/14; A61L 2101/06; A61L 2202/11; A61L 2202/17; A61L 2202/25; A61L 2209/11; A61L 2209/111; A61L 2209/13; A61L 2209/134; A61L 2209/14; C01B 11/08
See application file for complete search history.

(56) References Cited

U.S. PATENT DOCUMENTS

| | | | |
|---|---|---|---|
| 4,892,706 A | * | 1/1990 | Kralovic ............... A61L 2/18 |
| | | | 204/196.15 |
| 2006/0070959 A1 | | 4/2006 | Perkins et al. |
| 2007/0231247 A1 | | 10/2007 | Bromberg et al. |
| 2009/0208616 A1 | | 8/2009 | Perkins |
| 2010/0183745 A1 | | 7/2010 | Rossi et al. |

(Continued)

FOREIGN PATENT DOCUMENTS

WO     2013090540 A1     6/2013

OTHER PUBLICATIONS

ISA/US, International Search Report and Written Opinion for PCT Patent Application No. PCT/US2019/051612, dated Dec. 4, 2019, 5 pages.

(Continued)

*Primary Examiner* — Darren W Gorman
(74) *Attorney, Agent, or Firm* — NK Patent Law

(57) ABSTRACT

A system for creating and dispersing a dry fog utilizing a production system for producing hypochlorous acid, a preservation system for preserving hypochlorous acid, and a dry fog system for creating dry fog droplets of hypochlorous acid.

15 Claims, 9 Drawing Sheets

(56) References Cited

U.S. PATENT DOCUMENTS

Figure 1:
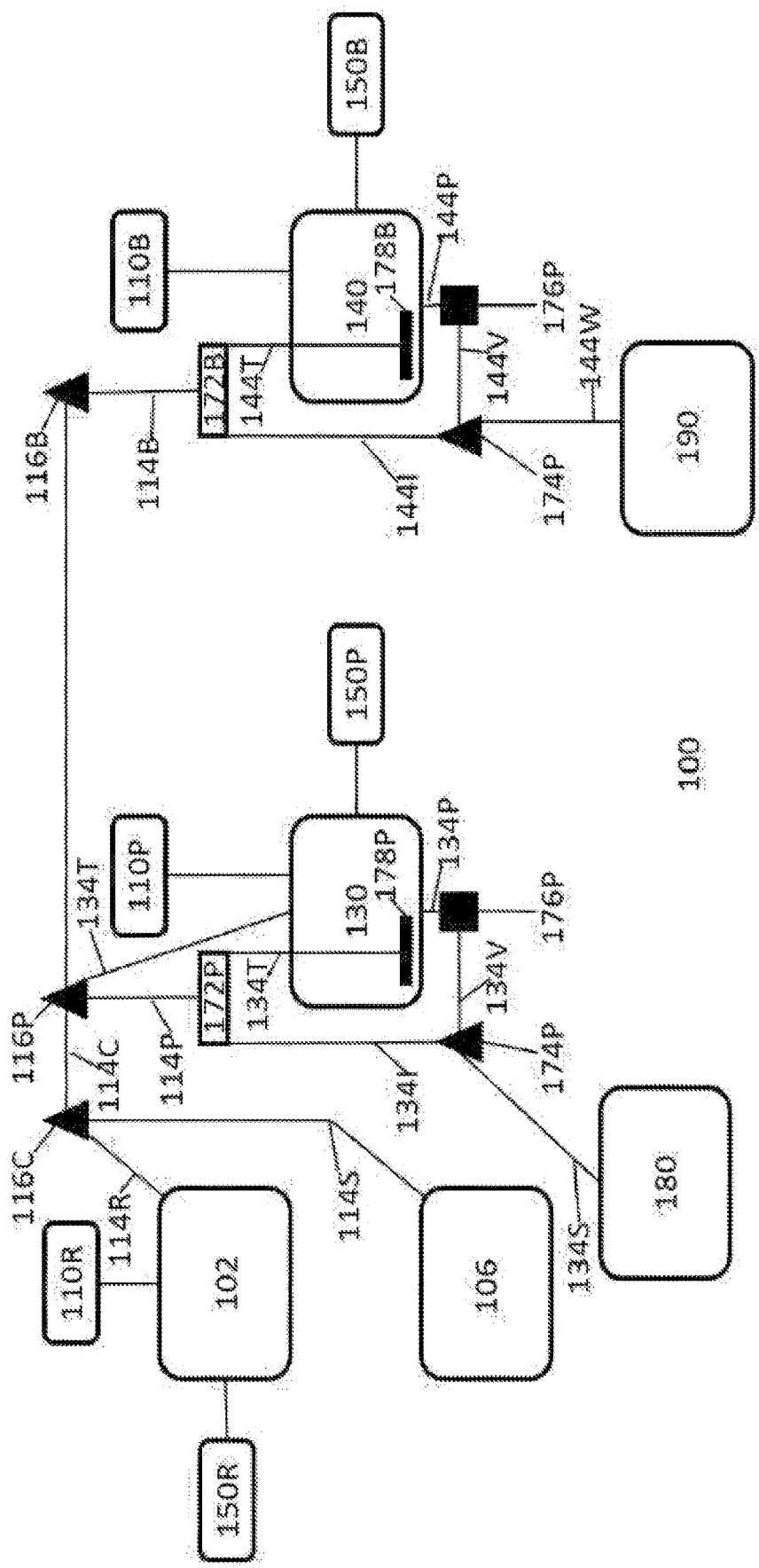
Figure 2:
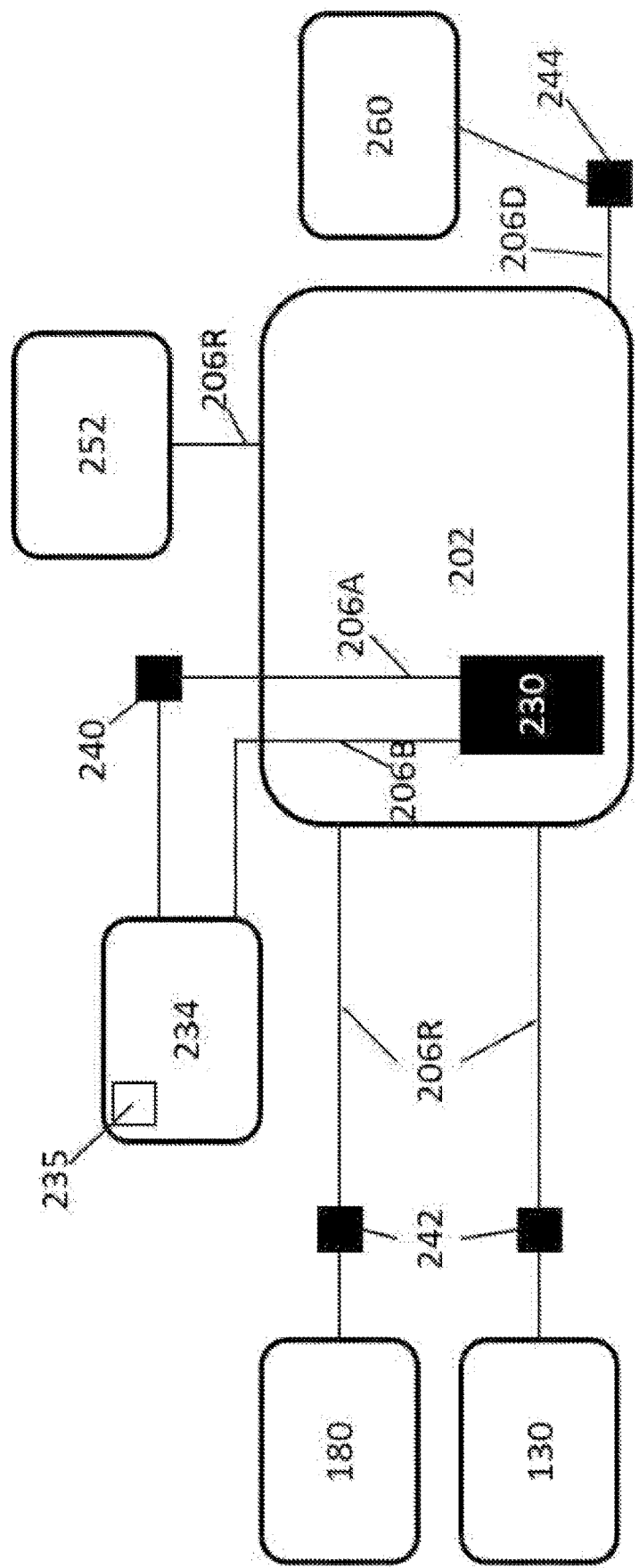

2013/0323375 A1   12/2013  Takahashi et al.
2017/0304475 A1*  10/2017  Frische .................... A61L 9/14
2018/0207302 A1   7/2018   Vasilenko

OTHER PUBLICATIONS

WIPO, International Preliminary Report on Patentability for PCT Patent Application No. PCT/US2019/051612, dated Mar. 9, 2021, 4 pages.

* cited by examiner

Enclosed space

- Aerosolized HOCl nano-particles
- Aerosolized HOCl micro-particles
- Chlorine gas
- Chlorine dioxide gas
- Air → micropartice collector and gas neutralizer system →

- Aerosolized HOCl nano-particles
- Air

Controller

Particle, RH, Cl₂ gas, ClO₂ gas sensors

- Aerosolized HOCl nano-particles
- Aerosolized HOCl micro-particles
- Chlorine gas
- Chlorine dioxide gas
- Air → Nanoparticle collector system →

- Chlorine gas (sometimes more than came in)
- Chlorine dioxide gas (sometimes more than came in)
- Air HOCl dry fog delivery system

FIG. 8

DRY FOG PRODUCTION AND APPLICATION METHODS AND SYSTEMS

CROSS-REFERENCE TO RELATED APPLICATIONS

This application is a continuation of PCT Patent Application No. PCT/US2019/051612 filed on Sep. 17, 2019, which claims priority to U.S. Provisional Patent Application No. 62/732,513 filed on Sep. 17, 2018 and U.S. Provisional Patent Application No. 62/732,512 filed on Sep. 17, 2018, the entire contents of all of which are incorporated by reference herein.

TECHNICAL FIELD

This disclosure is related to methods and systems for use with hypochlorous acid production, preservation, delivery and collection. The methods and systems described herein may be used in cleaning, sanitation and preservation of surfaces, spaces, objects and biological materials using a controlled dry fog dispersant.

BACKGROUND

Hypochlorous acid (HClO) is a weak acid that forms when chlorine dissolves in water. Hypochlorous acid and hypochlorite are oxidizers, and the primary disinfection agents of chlorine solutions, which are used prevalently in commercial operations handling biological materials or objects.

Dry fog delivery systems for hypochlorous acid solutions are generally used to sanitize or disinfect the air and surfaces in an enclosed space in a manner that doesn't moisten surfaces exposed to the particles. The delivery technologies of the prior art may range from specialized spray nozzles that emit a broad spectrum of particle sizes (see, e.g., U.S. Pat. No. 6,161,778 by James Haruch, which is herein incorporated by reference in its entirety) to vibrating mesh systems that produce uniformly sized particles (see, e.g., U.S. Pat. No. 8,555,874 to Fink, et al. and U.S. Pat. No. 10,335,558 to Boucher, et al., both of which are herein incorporated by reference in their entirety).

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

According to at least one embodiment, a system for creating and dispersing a dry fog is disclosed, the system comprising a production system for producing hypochlorous acid and a preservation system for preserving hypochlorous acid and a dry fog system for creating dry fog droplets of hypochlorous acid.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

FIG. 1 is a schematic view of the production system according to one or more embodiments of the present invention.

FIG. 2 is a schematic view of the preservation system according to one or more embodiments of the present invention.

FIG. 3 is flow diagram of the control unit maintaining a condition according to one or more embodiments of the present invention.

FIG. 4 is a schematic view of the dry fog delivery system according to one or more embodiments of the present invention.

FIG. 5 is a schematic view of the dry fog delivery system according to one or more embodiments of the present invention.

FIG. 6 is a flow diagram of the control unit operating the dry fog delivery system according to one or more embodiments of the present invention.

FIG. 7 is a free chlorine pH dissociation curve.

FIG. 8 is a schematic view of the collection system according to one or more embodiments of the present invention.

FIG. 9 is a schematic view of the particle collection system according to one or more embodiments of the present invention.

FIG. 10 is a perspective view of the particle collection system according to one or more embodiments of the present invention.

FIG. 11 is a schematic view of the gas collection system according to one or more embodiments of the present invention.

FIG. 12 is a perspective view of the gas collection system according to one or more embodiments of the present invention.

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies.

These descriptions may be presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions may be provided for exemplary purposes. Thus, not all embodiments within the scope of the drawings and these descriptions may be made according to such exemplary dimensions. The drawings may be not made necessarily to scale. Thus, not all embodiments within the scope of the drawings and these descriptions may be made according to the apparent scale of the drawings with regard to relative dimensions in the drawings. However, for each drawing, at least one embodiment is made according to the apparent relative scale of the drawing.

Solution Production System.

The production system 100 described herein may be used to create any numbers of solutions 10, including but not limited to the solutions 10 disclosed herein. Solutions 10 may also be acquired or produced using other methods described herein, including using solutions 10 created by the production system 100.

Production of one or more solutions 10 may involve mixing a gas 14 and production reagents 12P. In at least one embodiment, the hypochlorous acid (HOCl+NaCl+H2O) is a solution 10 produced, in part, by the mixture of a gas 14 being chlorine gas (Cl2) with production reagents 12P being sodium hydroxide (NaOH) and water (H2O).

According to one embodiment of the invention, the solution production system 100 may include a reaction tank 102 and/or storage tank 106 for delivering the gas 14 to a production tank 130 for creating a solution 10. In some embodiments including a reaction tank 102, excess or unwanted gas 14 may be delivered to a neutralizing tank 140 for elimination or conversion of the gas 14 to an innocuous neutralizing byproduct 22. The solution 10 may be delivered from the production tank 130 via a production solution hose 134S to a solution tank 180 for transport or to a preservation system 200 for preservation. The neutralizing byproduct 22 may be delivered from the neutralizing tank 140 via a neutralizing waste hose 144W to a waste tank 190 for disposal.

Solution Production System—Gas Production.

For the production of the gas 14, some embodiments of a solution production system 100 are reagent-based 100R, whereas other embodiments are gas-based 100G, and additional embodiments are a combination of the two 100C.

In a reagent-based embodiment of the production system 100R, two or more reaction reagents 12R may be mixed in a reaction tank 102 for forming a gas 14 along with one or more reaction byproducts 16R. In one embodiment, the reaction reagents 12R may be received by and mixed within a reaction tank 102 to form the gas 14. Additionally, the mixture of reaction reagents 12R may create one or more reaction byproducts 16R. The reaction tank 102 may be a sealed container having one or more sealable reagent reaction apertures 104R for receiving reaction reagents 12R for mixing and reacting. Each of the reagent reaction apertures 104R may be engageable, or in sealed engagement, with a reagent delivery system 110R for delivering reaction reagents 12R to the reaction tank 102. The reaction tank 102 may further include one or more gas reaction apertures 104G engageable, or in sealed engagement, with a gas-delivery system 112 for accepting and delivering gas 14 from the reaction tank 102. In one embodiment of the production system 100 which is reagent-based, the gas-delivery system 112 may include a reagent gas hose 114R passing through in a sealed engagement, or merely sealingly engaged to, a reagent reaction aperture 104R for accepting and delivering gas 14 therefrom. In another embodiment of the production system 100 which is gas-based, the gas-delivery system 112 may be selectively engaged with a gas storage tank 106 for accepting and delivering gas therefrom. The gas storage tank 106 may be pre-loaded with pressurized gas 14. The gas-based gas-delivery system 112 may include a storage gas hose 114S sealingly engaged to a storage aperture 108. In yet another embodiment of the production system, the gas-delivery system 112 may include both a reagent hose 114R engaged with an aperture 104R of the reaction tank 102 and a storage hose 114S engaged with an aperture 108 of the storage tank 106 for accepting and delivering gas selectively therefrom.

In some embodiments, two or more reaction tanks 102 may be included for fluidic engagement with a manifold for combining the gas 14 from the plurality of reaction tanks 102 into fluidic engagement with the reaction hose 114R.

As a safety precaution when the gas 14 may be considered harmful or undesirable, gas sensors 160G measuring gas 14 or gas derivates may be included in the system 1 (or production system 100) for monitoring the environment 3 for the presence of, or the concentration of, the gas 14 in the environment 3. The gas sensors 160G may engageable with the reaction tank 102, the storage tank 106, and/or another component of the system 1 and/or production system 100 or configured for placement in the environment 3.

Further, the one or more cleaning reaction apertures 104C of the reaction tank 102 may be engageable, or in sealed engagement, with one or more reaction cleaning systems 150R for delivering reaction cleaning solution(s) 152R and/or removing reaction byproducts 16R from the reaction tank 102. The cleaning reaction apertures 104C may be positioned on a nadir, a lower side/surface or a lower quarter of the reaction tank 102 (such a position allowing for heavier reaction byproducts 16R which have collected in the lower portion of the reaction tank to be retrieved without significant interaction with the gas 14).

In some embodiments, the reagent delivery systems 110 and/or the cleaning systems 150 of the solution production system 100 may include interchangeable stoppers for creating a sealed space within the reaction tank 102, 106, 130, 140. The reagent delivery and/or cleaning systems 110, 150 may include engageable funnels for delivering the reagent(s) 12 and/or cleaning solution(s) 152. While some funnels may be open, thereby temporarily creating an unsealed space within a tank 102, 106, 130, 140, other funnels may be pressurized and/or closed systems and include stoppers therewithin for a constant sealing of the reaction tank 102, 106, 130, 140 while the reagent(s) 12 and/or cleaning solution(s) 152 are being delivered. In other embodiments, these systems 110, 150 may include other sealed engagements, such as a mechanical delivery mechanism or an automated delivery mechanism, as available and known to those skill in the art. Similar systems and methods may be incorporated into delivery and cleaning systems for other tanks within the system 1.

EXAMPLE 1. In one embodiment of the system, the reaction reagents 12R may include hydrochloric acid (HCl) and sodium hypochlorite (NaOCl), which may be mixed for forming a gas 14 being chlorine gas (Cl2), along with reaction byproducts 16R water and salt. For example, at a ratio of two parts HCl to one part NaOCl for the reaction reagents 12R, the mixture in the reaction tank 102 will create one part gas 14 being chlorine gas, a two parts reaction byproducts 16R including one part salt and 1 part water (2HCl+NaOCl→H2O+Cl2+NaCl). Gas sensors 160G may be included to detect the gas 14 being chlorine gas or its derivative chlorine dioxide.

Any remaining chlorine gas may be neutralized by introducing sodium thiosulfate or a sodium thiosulfate compound using the reagent delivery system 110R and/or cleaning system 150R, thereby creating additional reaction byproducts 16R. The cleaning system 150R may further be utilized to remove reaction byproducts 16R and/or deliver cleaning solution(s) 152R into the reaction tank 102 for cleaning out any remaining byproducts 16R left unremoved. In some embodiments, the cleaning system 150R may include pressurized cleaning solution(s) 152R for removing particulate matter and/or precipitate from the reaction tank 102.

Solution Production System—Gas Delivery System.

The gas-delivery system 112 of the solution production system 100 may include one or more gas hoses 114R, 114S, 114D for accepting and delivering the gas 14 from the reaction tank 102 and/or storage tank 106 to the production tank 130 and/or neutralizing tank 140. In one embodiment, the reaction gas hose 114R accepting the gas 14 from the reaction tank 102 flows through and/or is sealingly engaged with a reaction aperture 104R positioned at an apex, an upper side/surface or an upper quarter of the reaction tank 102 (such a position allowing for the gas 14 which has collected in the upper portion of the reaction tank to be retrieved without significant interaction with the reaction reagents 12 or byproducts 16R). In another embodiment, the storage gas hose 114S may be sealingly engaged with a storage aperture 108 for accepting gas 14 from the storage tank 106. In a further embodiment, both a reaction gas hose 114R engaged with the reaction tank 102 and a storage gas hose 114S engaged with the storage tank 106 may be included in the gas-delivery system 112.

The gas-delivery system 112 may further include one or more pressure regulators 118 for regulating the pressure of the gas 14 from the reaction tank 102 and/or the storage tank 106. The reaction pressure regulator 118A may be positioned anywhere along the reaction gas hose 114A. The storage pressure regulator 118B may be positioned anywhere along the gas hose 114B. Although the pressure regulators 118 are depicted in the figures, some embodiments of the gas-delivery system 112 may not include pressure regulators 118A and/or 118B, as discussed below. The regulator(s) 118 may regulate pressure within a desired range. The desired range of pressure regulation may be 12-15, 10-20 or 1-50 pounds per square inch gauge, or may fall above or below these ranges.

The gas-delivery system 112 may further include one or more valves 116 for managing flow of the gas 14. For example, a combination gas valve 116C may engage both the reaction tank gas hose 114A and the storage tank gas hose 114B. The combination gas valve 116C may be configured for allowing gas 14 to pass from only one of the two tanks 102, 106 at a time onward through a combination gas hose 114C of the gas-delivery system 112. The combination gas hose 114C may extend from the combination gas valve 116C for delivering gas from the gas valve 116D towards the production tank 130 and/or neutralizing tank 140.

In other embodiments, whether reagent-based 100R, gas-based 100S or both 100C, the gas-delivery system 112 may include a production valve 116P for managing flow from the reaction tank 102 and/or storage tank 106 to the production tank 130. The production valve 116P may be positioned along the reaction tank gas hose 114R in a reagent-based production system, the storage tank gas hose 114S in a gas-based production system, or may be positioned along a combination tank gas hose 114C in a combination reagent and gas-based system.

In reagent-based or combination production system embodiments, the gas delivery system 112 may include a neutralizing valve 116B for managing flow from the reaction tank 102 to the neutralizing tank 140. The neutralizing valve 116B may be positioned along the reaction tank gas hose 114R in a reagent-based production system, or may be positioned along a combination tank gas hose 114C in a combination reagent and gas-based system.

In reagent-based or gas-based production systems 100R, 100S, the reaction gas hose 114R or the combination gas hose 114C of the gas-delivery system 112 may include a splitter 115 distal the reaction tank 102 for splitting the reaction or combination hose 114R, 114C into two hose lines—a first hose 114Y and a second hose 114Z—for engagement with the production valve 116P and neutralizing valve 116B, respectively. In other embodiments, a single valve 116 may operate as both the production valve 116P and the neutralizing valve 116B. The injector 172P, 172B may be sealingly engaged to an production injector hose 114P or a neutralizing injector hose 114B for delivering the gas 14 from the production gas valve 116P or neutralizing gas valve 116B to the production injector 172P or neutralizing injector 172B, respectively.

In some embodiments, the reaction hose 114R, storage hose 114S or combination hose 114C may flow directly through, and in sealed engagement with, the injector aperture 132I of the production tank 130 for delivering gas 14 directly into the production tank 130. The hose 114R, 114S, 114C may include a diffuser 178P for diffusing gas 14 within the production reagents 12P of the production tank 130.

Solution Production System—Production Tank.

In various embodiments of the solution production system 100, the production tank 130 may include reagent production apertures 132R engageable, or in sealed engagement, with production reagent delivery system(s) 110P for delivering production reagents 12P to the production tank 130. Delivery systems 110 are further discussed above. In addition to the production reagent delivery systems 110P, the production tank 130 may be sealingly engaged with a production injection system 170P for delivering and incorporating the gas 14 into the production tank 130. The injection system 170P may include a production injector 172P, a production flow valve 174P, a production pump 176P, and/or a plurality of production hoses 134. Flow valves 174 are further discussed above.

The production pump 176P may be sealingly engaged with the tank 130 via a pump hose 134P for initially drawing out and accepting the reagent(s) 12P previously and/or concurrently received by the tank 130 through the reagent delivery system 110P. The pump hose 134P may be sealingly engaged with a production pump aperture 132P which may be positioned on a nadir, a lower side/surface or a lower quarter of the production tank 130 (such a position allowing for reagent(s) 12P which have collected in the lower portion of the production tank 130 to be retrieved). If the production pump 176P is self-priming, it may be positioned on an upper half of the production tank 130, with the pump hose 134P extending to the nadir or lower quarter of the production tank 130. The reagent(s) 12P drawn out by the pump hose 134P may be delivered through the pump 176P and towards the flow valve 174P through a flow hose 134F sealingly engaged with both the pump 176P and the flow valve 174P.

The production flow valve 174P of the injection system 170P may be additionally sealingly engaged to a production injector hose 134I for delivering the reagent(s) 12P from the flow valve 174P to the injector 172P. The injector 172P may further be sealingly engaged to an injector hose 114P for delivering the gas 14 from the production gas valve 116P to the injector 172P. The injector 172P may receive both the gas 14 from the gas valve 116P and the reagent(s) 12P from the tank 130 and mixing them together for ejection. In some embodiments, the injector 172P may receive the gas 14 from the production gas valve 116P and the reagent(s) 12P directly from the production reagent delivery system 110P, the delivery system 110P being sealingly engaged with the injector 172P or an additional valve 188 in fluid communication with the injector 172P. The production injectors 172P (as well as the neutralizing injectors 172B) disclosed herein may include any injector or mixer of the prior art, including but not limited to gas-liquid venturi injectors/mixers such as those depicted in U.S. Pat. Nos. 6,192,911 and 9,636,715 to Ronald Barnes, which are incorporated herein by reference in their entirety. When venturi injectors are included in the system 1, the venturi effect may create pressures to pull gas and/or liquids to the injectors.

The production mixture 20P (of the gas 14 and the reagent(s) 12P delivered to, and drawn from, the production tank 130) may be delivered from the production injector 172P to the production tank 130 through a production tank hose 134T. The production tank hose 134T may be sealingly engaged with the production injector 172P and extend through, in a sealed engagement, the injector production aperture 132I of the production tank 130. The production tank hose 134T may extend along the height of the production tank 130 to the lower portion of the production tank 130, proximal a lower side or nadir of the tank 130. The production tank hose 134T may be engaged with a production diffuser 178P for introducing the gas 14 for dissolution into the reagent(s) 12P and/or the production mixture 20P in the production tank 130. The production tank 130, the production tank hose 134T and/or the production diffuser 178P may take any number of shapes and forms. In one embodiment, the production tank 130 may be conical or trapezoidal with the upper portion being smaller in width than the lower portion, thereby extending the length by which the production mixture 20P must travel from the production diffuser 178P to the upper portion of the production tank 130, thereby increasing the likelihood that the gas 14 reacts with the reagent(s) 12P.

Following and/or concurrently with the creation and delivery of gas 14 from the reaction tank 102, and/or delivery of gas 14 from the storage tank 106, the production gas valve 116P may be opened for delivery of gas 14 to an inlet of the production injector 172P for the initial mixture of gas 14 with the production reagent(s) 12P cycling through the injector 172P. Once delivered through the production diffuser 178P via the production tank hose 134T, the gas 14 may further mix with the production reagent(s) 12P housed in the production tank 130 to create the solution 10 and/or production byproducts 16P. Meanwhile, the production pump 176P may draw further production reagent(s) 12P, gas 14 (and the resulting production mixture 20P) from the production tank 130, through the valve hose 134V and to the injector 172P for continued mixing with the gas 14.

This cycle may continue until the production tank 130, solution 10, and/or production mixture 20P fall within certain conditions 2. Sensors 160 inserted into and/or housed within the production tank 130 and/or production injection system 170P may sense actual conditions 22 for permitting determination of whether the conditions 2 of the production mixture 20P and/or solution 10 have been reached. For example, the conditions 2 may include a range for pH, pressure, temperature and/or chemical molarities or concentrations. Sensors, such as a pH sensor 160P, temperature sensor 160T and/or concentration sensor 160C, sensing the actual conditions 22 may permit manual and/or automatic shut off or turn on of any number of valves 116, 174, 188. In one embodiment, once the production mixture 20P, including the solution 10, is within a certain pH range, the production gas valve 116P may be closed, the production pump 176P may be turned off, and/or the production flow valve 174P may be closed.

In one embodiment, the sensors 160 may be used to sense actual conditions 22 of the production reagent(s) 12P before the gas 14 is introduced to the production tank 130. The conditions 2 of the production reagent(s) 12P may correspond to a target concentration and/or pH of the solution 10 and/or production mixture 20P.

Once the solution 10 has been produced or the production mixture 20P and/or solution 10 has reached a target concentration, pH or other specified property, the valves 116, 174, 188 and/or pumps 176 may be manipulated to control flow of gas 14, mixture 20 and/or solution 10 within the system 100. In one embodiment, the production gas valve 116P may be turned off, ceasing flow of gas 14 to the production tank 130. The production flow valve 174P may be actuated to cease flow of the production mixture 20P and/or solution 10 to the injector production hose 134I. In some embodiments, the production pump 176P may be activated (or remain in activation) and the production flow valve 174P may be actuated to enable fluid communication with a release production hose 134R for withdrawing the mixture 20P and/or solution 10 from the production tank 130 and into a solution tank 180 for storing the mixture 20P and/or solution 10.

A production cleaning system 150P may be engaged with a production cleaning aperture 132C of the production tank 130. As described herein, a cleaning system 150 generally may deliver cleaning solution(s) 152, such as a production cleaning solution 152P, for neutralizing, removing and/or cleaning a tank 102, 106, 130, 140.

EXAMPLE 2. In one embodiment of the invention, the method of producing a solution 10 being hypochlorous acid (HOCl) using the production system 100 includes the production injector receiving a gas 14 being chlorine gas (Cl2) and the production tank 130 receiving sodium hydroxide (NaOH) and water (H2O) production reagents 12P (or receiving a sodium hydroxide solution as a reagent 12P). In such an embodiment, the sodium hydroxide solution (NaOH+H2O) will continually mix with the chlorine gas (Cl2) by the cycling through the production injection system 170, creating the solution 10 hypochlorous acid (HOCl), as well as production byproducts 16P intermediate hydrochloric acid (HCl), an intermediate byproduct, and salt (NaCl) and water, final byproducts (NaOH+Cl2+H2O→NaOH+HOCl+HCl→NaCl+H2O+HOCl), as the sodium hydroxide (NaOH) continues to react with the chlorine gas (Cl2) and the hydrochloric acid (HCl).

Introducing, for example, a sodium hydroxide solution with a pH of 12.59 (as sensed by a pH sensor 160P positioned within the production delivery system 110P and/or production tank 130) produces a hypochlorous acid (HOCl) concentration of 2200 ppm at 6 pH (as sensed by a pH sensor 160P within the production injection system 170P and/or production tank 130). Referring to the free chlorine pH dissociation curve, the mixture of chlorine gas (Cl2) and the sodium hydroxide solution with a pH of 12.59 will initially create OCl—, and Na+, and as the NaOH is reduced and the OH is neutralized, the Na+ becomes more attracted to the H, the HOCl concentration increases as the pH lowers.

In some prior art systems, electrolysis of a diluted water-sodium chloride solution passing through on electrolysis chamber facilitates the conversion of chloride ions and water molecules into chlorine oxidants (chlorine gas, hypochlorous acid, and hypochlorite ion) within the anode chamber. Unlike the presently disclosed invention, various electrolytic byproducts may be created that eventually may interact with the HOCl (e.g., HO-hydroxyl radicals, HO2— -peroxide anion, O2-singlet molecular oxygen, O2— -superoxide-anion, O3-ozone, O-atomic oxygen, HClO2-chlorous acid, ClO— -hypochlorite-ion, ClO-hypochlorite-radical, ClO2- chlorine dioxide, and/or HCl-hydrochloric acid). The presently disclosed systems and methods enable minimization of these electrolytic byproducts, if not total elimination, by avoiding electrolysis and by enabling more pure chemical interactions at lower temperatures, such as room temperature. Sodium hydroxide (NaOH) and water may be mixed to create the sodium hydroxide solution, resulting in a much cleaner and more precise concentrations that many of the prior art systems. A specific concentration of HOCl in parts per million (ppm) may be produced when the pH of the gas/reagent mixture 20P in the production tank 130 drops to a pH around 6.

Upon production of the desired amount or quantity of hypochlorous acid, any excess sodium hypochlorite in the production tank 130 may be neutralized by the addition of sodium thiosulfate (or additionally a sodium hydroxide solution) from the production cleaning system 150P to the production tank 130 ($Na_2S_2O_3 + 4NaOCl + 2NaOH \rightarrow 2Na_2SO_4 + H_2O + 4NaCl$), thereby halting the production of chlorine gas, leaving only salt (NaCl) and sodium sulfates ($Na_2SO_4$), which are both highly soluble in water. Water may be added by the cleaning system 150P until the production tank 130 is flushed and specified cleaning conditions 2 with the production tank 130 are reached.

Solution Production System—Neutralizing Tank.

Any excess solution 10, reagents 12, gas 14, byproducts 16, mixtures 20 and/or cleaning solutions 152 in the reaction tank 102, storage tank 106, production tank 130, reagent delivery systems 110, gas delivery systems 112, cleaning systems 150 and/or injection systems 170 may be transported to one or more neutralizing tanks 140. Neutralizing tanks 140 may be useful for neutralizing any solution 10, reagents 12, gas 14, byproducts 16, mixtures 20 and/or cleaning solutions 152 that may be considered harmful or undesirable. The neutralizing gas valve 116B may be actuated to open to permit flow of gas 14 into the neutralizing tank 140. The production tank 130 may further include an excess hose 134E for removing any excess gas 14 for eventual transportation to the neutralizing tank 140. Transportation to the neutralizing tank 140 may be effectuated using any number of hoses 114, 134, 144, pumps 176 and/or valves 116, 174, 188 of the system 100. In some embodiments additional hoses 184, additional pumps 186 and additional valves 188 may be configured for permitting direct transport from reaction tank 102, storage tank 106, production tank 130, reagent delivery systems 110, gas delivery systems 112, cleaning systems 150 and/or injection systems 170 to the neutralizing tank 150 using the methods and systems described herein and/or disclosed in the prior art.

In further embodiments, any excess solution 10, reagents 12, gas 14, byproducts 16, mixtures 20 and/or cleaning solutions 152 may be withdrawn and transported through the neutralizing injection system 170.

Any solution 10, reagents 12, gas 14, byproducts 16, mixtures 20 and/or cleaning solutions 152 received into, or subsequently produced within, the neutralizing tank 140 may be labeled a neutralizing mixture 20B.

In reagent or combination systems 100R, 100C, the neutralizing tank 140 may include reagent neutralizing apertures 142B engageable, or in sealed engagement, with neutralizing reagent delivery system(s) 110B for delivering neutralizing reagents 12B to the neutralizing tank 130. Delivery systems 110 are further discussed above.

In addition to the neutralizing reagent delivery systems 110B, the neutralizing tank 140 may be sealingly engaged with one or more neutralizing injection systems 170B for delivering and incorporating the gas 14 (or neutralizing mixture 20B) into each the neutralizing tank 140. Each injection system 170B may include a neutralizing injector 172B, a neutralizing flow valve 174B, a neutralizing pump 176B, and/or a plurality of neutralizing hoses 144. Flow valves 174 are further discussed above.

The neutralizing pump 176B may be sealingly engaged with the neutralizing tank 140 via a pump hose 144P for initially drawing out and accepting the neutralizing reagent(s) 12B previously and/or concurrently received by the neutralizing tank 140 through the neutralizing reagent delivery system 110B. The neutralizing pump hose 144P may be sealingly engaged with a neutralizing pump aperture 142P which may be positioned on a nadir, a lower side/surface or a lower quarter of the neutralizing tank 140 (such a position allowing for reagent(s) 12B which have collected in the lower portion of the neutralizing tank 140 to be retrieved). The reagent(s) 12B drawn out by the pump hose 144P may be delivered through the pump 176B and towards the flow valve 174B through a neutralizing flow hose 144F sealingly engaged with both the pump 176B and the flow valve 174B.

The neutralizing flow valve 174B of the neutralizing injection system 170B may be additionally sealingly engaged to a neutralizing injector hose 144I for delivering the reagent(s) 12B from the flow valve 174B to the injector 172B. The injector 172B may further be sealingly engaged to an injector hose 114B for delivering the gas 14 (or neutralizing mixture 20B) from the neutralizing gas valve 116B or the additional valve 188 to the neutralizing injector 172B. The injector 172B may be capable of receiving both the gas 14 from the gas valve 116B (or the neutralizing mixture 20B from the additional valve 188) and the reagent(s) 12B from the tank 140 and mixing them together for ejection. In some embodiments, the injector 172B may receive the gas 14 (or the neutralizing mixture 20B) from the production gas valve 116B (or the additional valve 188) and the reagent(s) 12B directly from the neutralizing reagent delivery system 110B, the delivery system 110B being sealingly engaged with the injector 172B or an second additional valve 188 in fluid communication with the injector 172B.

The neutralizing mixture 20B may be delivered from the neutralizing injector 172B to the neutralizing tank 130 through a neutralizing tank hose 144T. The neutralizing tank hose 144T may be sealingly engaged with the neutralizing injector 172P and extend through, in a sealed engagement, the injector neutralizing aperture 142I of the neutralizing tank 140. The neutralizing tank hose 144T may extend along the height of the neutralizing tank 130 to the lower portion of the neutralizing tank 140, proximal a lower side or nadir of the tank 140. The neutralizing tank hose 144T may be engaged with a neutralizing diffuser 178B for introducing the gas 14 (or neutralizing mixture 20B) for dissolution into the reagent(s) 12B and/or another neutralizing mixture 20B in the neutralizing tank 140. The neutralizing tank 140, the neutralizing tank hose 144T and/or the neutralizing diffuser 178B may take any number of shapes and forms. In one embodiment, the neutralizing tank 140 may be conical or trapezoidal with the upper portion being smaller in width than the lower portion, thereby extending the length by which the neutralizing mixture 20B must travel from the neutralizing diffuser 178B to the upper portion of the neutralizing tank 140, thereby increasing the likelihood that the gas 14 (or the neutralizing mixture 20B) reacts with the reagent(s) 12B.

Following and/or concurrently with delivery of gas 14 (or neutralizing mixture 20B), the neutralizing gas valve 116B (or additional valve 188) may be opened for delivery of gas 14 (or neutralizing mixture 20B) to the neutralizing injector 172B for the initial mixture of gas 14 (or neutralizing mixture 20B) with the neutralizing reagent(s) 12B (and/or the additional neutralizing mixture 20B). Once delivered through the neutralizing diffuser 178B and/or the neutralizing tank hose 144T, the gas 14 (or neutralizing mixture 20B) may further mix with the neutralizing reagent(s) 12B (and/or neutralizing mixture 20B) housed in the neutralizing tank 140 to create the neutralizing byproducts 16B. Meanwhile, the neutralizing pump 176B may draw additional neutralizing reagent(s) 12B, gas 14 (and the resulting solution 10 and byproducts 16B) from the neutralizing tank 140, through the valve hose 144V and to the injector 172B for continued mixing.

This cycle may continue until the actual conditions 22 within the neutralizing tank 140 and/or the neutralizing byproducts 16B fall within the conditions 2. Sensors 160 inserted into and/or housed within the neutralizing tank 140 and/or neutralizing injection system 170B may sense the actual conditions 22 for permitting determination of whether the conditions 2 of the neutralizing mixture 20B have been reached. For example, the conditions 2 may include a range for pH, pressure, temperature and/or chemical molarities or concentrations. Sensors, such as a pH sensor 160P, temperature sensor 160T and/or concentration sensor 160C, sensing the actual conditions 22 may permit manual and/or automatic shut off or turn on of any number of valves 116, 174, 188. In one embodiment, once the neutralizing mixture 20B is within a certain pH range, the neutralizing gas valve 116B may be closed, the neutralizing pump 176B may be turned off, and/or the neutralizing flow valve 174B may be closed.

In one embodiment, the sensors 160 may be used to sense actual conditions 22 of the neutralizing reagent(s) 12B before the gas 14 or neutralizing mixture 20B is introduced to the neutralizing tank 140. The conditions 2 of the neutralizing reagent(s) 12B may correspond to a target concentration and/or pH of the neutralizing mixture 20B.

Once the neutralizing mixture 20B and/or solution 10 has reached a target concentration, pH or other specified property, the valves 116, 174, 188 and/or pumps 176 may be manipulated to control flow of gas 14, mixture 20 and/or solution 10 within the system 100. In one embodiment, the neutralizing gas valve 116B or additional valve 188 may be turned off, ceasing flow of gas 14 or the neutralizing mixture 20B to the neutralizing tank 140. The neutralizing flow valve 174B may be actuated to cease flow of the neutralizing mixture 20B to the injector neutralizing hose 144I. In some embodiments, the neutralizing pump 176B may be activated (or remain in activation) and the neutralizing flow valve 174B may be actuated to enable fluid communication with a release neutralizing hose 144R for withdrawing the mixture 20B from the neutralizing tank 140 and into a waste tank 190 for storing the mixture 20B.

A neutralizing cleaning system 150BP may be engaged with a neutralizing cleaning aperture 142C of the neutralizing tank 140. As described herein, a cleaning system 150 generally may deliver cleaning solution(s) 152, such as a neutralizing cleaning solution 152B, for neutralizing, removing and/or cleaning a tank 102, 106, 130, 140, 180, 190.

EXAMPLE 3. In one embodiment of the invention, the method of producing a solution 10 being hypochlorous acid (HOCl) using the reagent-based system 100R or combination system 100C includes transporting and neutralizing excess chlorine gas (Cl2) in the neutralizing tank 140 once the production of the desired amount or quantity of hypochlorous acid (the solution 10) is achieved. Any excess chlorine gas in the reaction tank 102 may be transported to the neutralizing tank 140. The neutralizing reagents 12B received by the neutralizing injector 172B and/or neutralizing tank 140 from the neutralizing reagent delivery system 110 may be sodium hydroxide or a sodium hydroxide solution, thereby converting the chlorine gas to a hypochlorous acid solution (NaOH+Cl2+H2O→NaCl+H2O+HOCl) and or sodium hypochlorite solution (2NaOH+Cl2→NaCl+NaOCl+H2O). A pH sensor 160P may be utilized to determine which neutralizing reagent 20B to use by referencing the pH sensed property to the free chlorine pH dissociation curve. The hypochlorous acid or sodium hypochlorite created may be a result of the alkaline solution of water and sodium hydroxide reacting with the chlorine gas being injected into the neutralizing tank.

Any hypochlorous acid and/or sodium hypochlorite in the neutralizing tank 140 may be diverted to the waste into a waste tank 190 or remain in the neutralizing tank 140 for neutralization with neutralizing reagents 12B water, sodium thiosulfate and sodium hydroxide. These neutralizing reagents 12B may be combined with HOCl and undergo multiple reactions with free and combined chlorine, depending on the solution pH. The amount of sodium thiosulfate desired for neutralization will vary with the solution pH sensed. Any hydrochloric acid produced may be salted out by the sodium hydroxide (HCl+NaOH→NaCl+H2O).

In one embodiment, the HOCl neutralization involves the following: Na2S2O3+4HOCl+H2O→2Na2SO4+4HCl; Na2S2O3+HOCl→Na2SO4+S+HCl; 2Na2S2O3+HOCl→Na2S4O6+NaCl+NaOH.

In another embodiment, NaOCl neutralization involves the following: Na2S2O3+4NaOCl+2NaOH→2Na2SO4+H2O+4NaCl In a further embodiment, the hypochlorous acid stored in the waste tank 190 or the neutralizing tank 140 may be mixed with sodium thiosulfate and sodium hydroxide solution, after which the waste tank 190 or neutralizing tank 140 may be sealed and shaken for a duration (e.g., 10-30 seconds, 20 seconds or some other range).

Preservation of Hypochlorous Acid.

According to further embodiments of the disclosed system 1, once a solution 10 is produced by the production system 100, or acquired or stored via other means, a preservation system 200 and methods of use may preserve the solution 10. The preservation system 200 may include a preservation tank 202 for storing and preserving the solution 10. In some embodiments of the system 1, the preservation tank 202 of the preservation system 200 is the same solution tank 180 of the production system 100 and may be engaged to both systems 100, 200 and incorporated for use in each system 100, 200 accordingly. In other embodiments, the solution tank 180 may be disengaged and sealed from the production system 100 for transportation and engagement with the preservation system 200 for use as a preservation tank 202 therein. In other embodiments, the solution tank 180 and/or another solution tank 181 may be in engageable with the preservation tank 202.

The preservation tank 202 may include an reception preservation aperture 204R for receiving the solution 10 from a reception preservation hose 206R in sealed and fluidic engagement with a solution tank 180, another solution tank 181 and/or another receptacle housing the solution 10. Due to instability of many solutions 10, the tanks 180, 181, 202, as is more fully described above, may be configured, amended and/or manufactured for blocking ultraviolet light or sunshine, minimizing contact with environmental air, controlling the temperature and/or minimizing adverse interactions with the tank 180, 181, 202 components and/or surfaces.

To measure when the solution 10 is within a temperature range, the preservation system 200 and/or preservation tank 202 may include a temperature sensor 210T for sensing a temperature of the solution 10 and/or within the preservation system 200 or tank 202. The temperature sensor 210T may be positioned within or on the preservation system 200 and/or preservation tank 202 or may insertable therewithin.

To measure when the solution 10 is within a pH range, the preservation system 200 and/or preservation tank 202 may include a pH sensor 210P for sensing a pH of the solution 10 and/or within the preservation system 200 or tank 202. The pH sensor 210P may be positioned within or on the preservation system 200 and/or preservation tank 202 or may insertable therewithin.

To measure when the solution 10 is within another property or condition range, the preservation system 200 and/or preservation tank 202 may include one or more other sensors 160, 210 for sensing a property or condition of the solution 10 and/or within the preservation system 200 or tank 202. The one or more sensors 160, 210 may be positioned within or on the preservation system 200 and/or preservation tank 202 or may insertable therewithin. For example, gas sensors 160G may be included proximal to, and outside of, the preservation tank 202 for measuring the concentration of gas 14 in the environment about the tank 202. One or more of the sensors 160, 210 may be housed together. Additional sensors 160, 210 and their uses are described further herein and may be applied to the preservation system 200.

The preservation system 200 may further include an immersion coil 230 housed within, or insertable within, the preservation tank 202. The immersion coil 230 may define an entry 230A for receiving immersion fluid 232 and an exit 230B from which the immersion fluid 232 may be withdrawn. The preservation system 200 may further include am immersion tank 234 for housing a portion of the immersion fluid 232. The immersion tank 234 may include a refrigeration unit 235 for controlling and maintaining an immersion temperature or range of the immersion fluid 232 within the immersion tank 234. The immersion coil 232 may be made of titanium or stainless steel or another non-reactive material. The chilling fluid 238 may be a concentrated sodium hydroxide (NaOH) solution.

An immersion entry hose 206A may be sealingly engaged with both an immersion exit aperture 238A of the immersion tank 234 and the coil entry 230A for enabling fluidic communication therebetween, the immersion entry hose 206A flowing through, and in sealed engagement with, an entry aperture 204A of the preservation tank 202. An immersion exit hose 206B may be sealingly engaged both with an immersion entry aperture 238B of the immersion tank 234 and the coil exit 230B for enabling fluidic communication therebetween, the immersion exit hose 206B flowing through, and in sealed engagement with, an exit aperture 204B of the preservation tank 202. The cycling of the immersion fluid 232, and the fluidic rate of the cycling, through the immersion tank 234, immersion coil 230 and hoses 206A, 206B may be effectuated by an immersion pump 240 positioned along one of the hoses 206A, 206B.

Though the solution 10 is stored within the preservation tank 202, and certain adverse conditions are avoided, such as exposure to light, ambient air, extreme pH levels and undesired temperatures, the solution 10 may still be predisposed to decomposition over time. To counteract or minimize the decomposition of the solution 10, the preservation tank 202 may include a preservation reagent aperture 204P for engagement with a preservation reagent hose 206P for delivering a preservation reagent 250 to the preservation tank 202. The reagent hose 206P may be in sealed engagement with a preservation reagent tank 252 and/or the immersion tank 234. In embodiments where the immersion fluid 232 may also serve the function of a preservation reagent 250, the immersion tank 234 may define a delivery aperture 238C for engaging the reagent hose 206P. A delivery pump and/or valve 242 may be included along the reagent hose 206P for managing the titration or flow rate of the reagent 250 from the preservation reagent tank 252 and/or immersion tank 234.

In some embodiments, the preservation tank 202 may also define a dispensing aperture 204D through which a dispensing hose 206D may pass in sealed engagement thereto. One end of the dispensing hose 206D may be positioned on a nadir, a lower side/surface or a lower quarter of the preservation tank 202 (such a position allowing for solution 10 which as collected in the lower portion of the preservation tank 202 to be retrieved). A dispensing pump 244 may be engaged with dispensing hose 206D for managing and controlling the fluid flow of the solution 10 from the preservation tank 202. The dispensing hose 206D may be sealably engaged with a preserved solution tank 260 for storing and/or transporting the solution 10.

The various sensors 160, 210, various pumps 240, 242, 244 and/or the refrigeration unit 235 may be in electronic communication with a preservation control unit 220. In other embodiments, the various sensors 160, 210, various pumps 240, 242, 244 and/or the refrigeration unit 235 may be manually operated. In yet other embodiments, some of these components may be manually operated and others may be automatically and/or electronically operated. The preservation control unit 220 may include a number of sub-control units in electronic communication, a display panel, operational controls and/or wireless communication features for operation, as described herein.

In one embodiment of the preservation system 200, a method of maintaining a preservation condition 270 for the solution 10, preservation system 200 and/or preservation tank 202 is provided. The preservation condition 270 may include a value or a specific range of values for one or more specific conditions (e.g., temperature, pH, humidity, time, concentration, etc.). One or more of the sensors 160, 210 may be employed to measure various conditions 2 of the system 1, environment 3, solution 10, preservation system 200 and/or preservation tank 202. An actual preservation condition 272 may be directly measured or may be calculated or determined by the control unit 220 using one or more of the other conditions 2. If the actual preservation condition 272 matches, or falls within, the preservation condition 270, the preservation system 200 may remain unchanged for a waiting period 274. If the actual preservation condition 272 does not match, or falls without, the preservation condition 270, one or more components of the preservation system 200 may be changed through an action 4.

Figure 3:
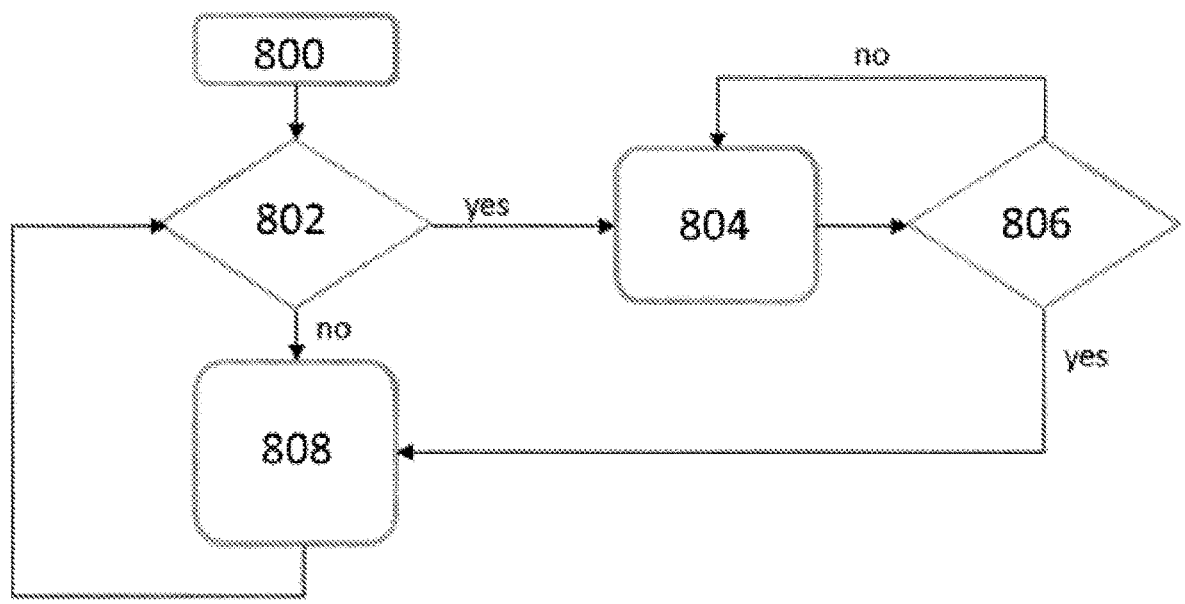
Figure 4:
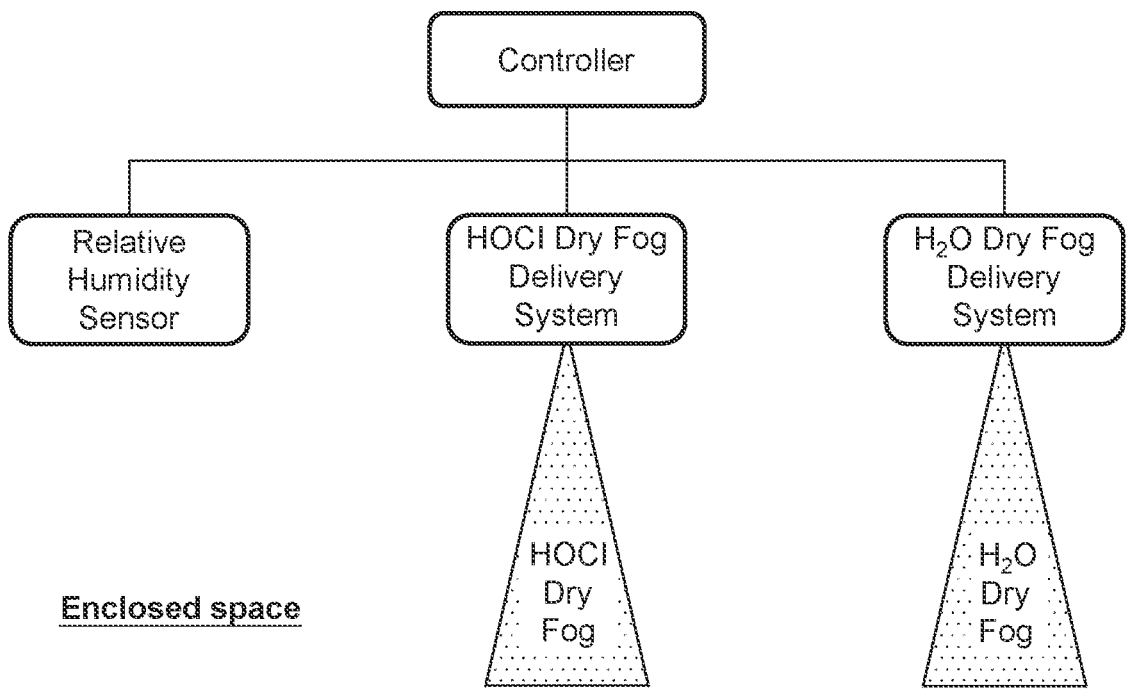
Figure 5:
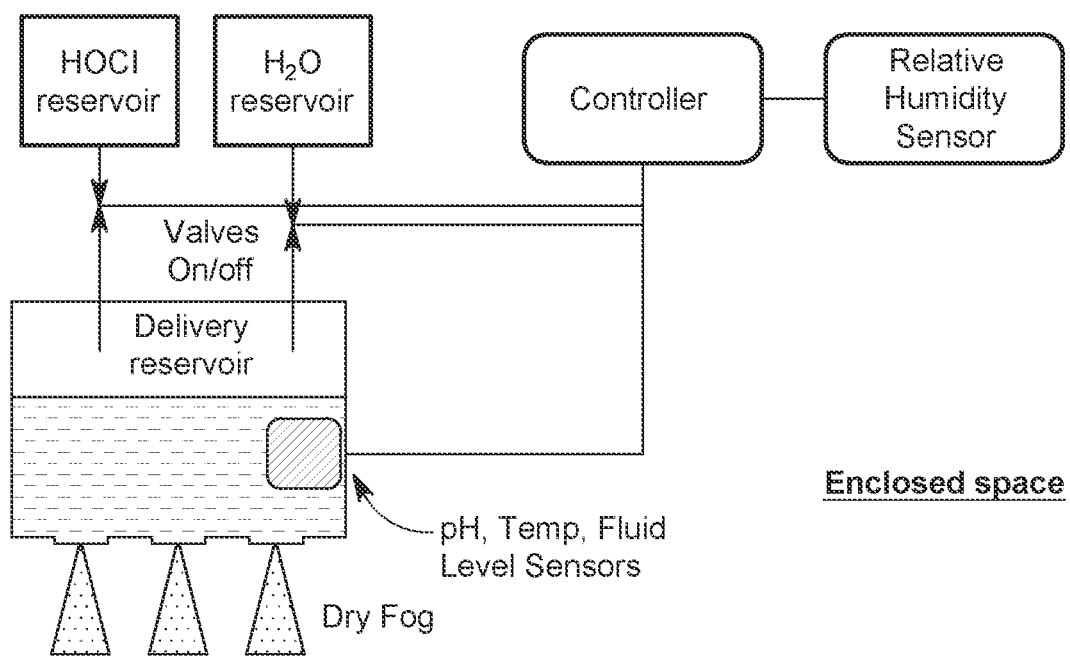

In the embodiment of FIG. 3, the system 1 may start 800, determine if the pH is less than 5.95 802. If yes, then add NaOH solution 804, then determine if the pH is greater than 6.05 806. If yes, then wait for a specified period of time 808.

For example, if the preservation condition 270 is a pH range for the solution 10 and the actual condition 272 is outside the pH range, the delivery pump 242 may be activated for delivering a quantity of preservation reagent 250 to the preservation tank 202 in an attempt to bring the measured pH of the solution 10 within range. Following the action 4 being the pump activation, a waiting period 274 may pass before the actual condition 272 is measured or determined again. If the actual condition 272 is outside the pH range again, the delivery pump 242 may be activated again (i.e., another action 4 is taken) and a waiting period 274 may again pass. If the actual condition 272 then falls within the preservation condition 270 being the pH range, the action 4 may not be taken, and the waiting period 274 again may pass. These methods steps may be performed for any length of time to ensure that the preservation condition 270 is maintained so that the decomposition of the solution 10 is minimized.

The same method steps may be used for any number of preservation conditions 270. In another example, the preservation condition 270 may be a temperature range for the preservation tank 202 and the action may be to activate the immersion pump 240 for cycling immersion fluid 232 through the immersion coil 230 housed within the solution 10. The action 4 may be predefined and may correspond to the actual preservation condition 272 so that the action 4 taken is relative to the difference between the actual condition 272 and the preservation condition 270.

EXAMPLE 4. According to further embodiments of the disclosed invention, once a solution 10 being hypochlorous acid (HOCl) is produced, methods and systems may be deployed to preserve it. Hypochlorous acid is an unstable molecule that readily decomposes into hydrochloric acid and oxygen (2HOCl→2HCl+O2). Hypochlorous acid is unstable against ultraviolet light, sunshine, contact with air, elevated temperatures above 25° C., and is rapidly consumed by numerous organic compounds and/or inorganic ions. Hypochlorous acid solution with a high FAC count (—ppm) (1000+) decays rapidly at room temperature. Without intervention, the FAC count (—ppm) will decay significantly and within a few days a solution with a pH of 6.5 will drop below 4.5. At this point the solution becomes hazardous to be around given that it is releasing chlorine gas (Cl2). The release of chlorine gas (Cl2) may also accelerate since some of the Cl2 may create more hydrochloric acid, which further decreases the pH while also increasing the rate of chlorine gas release by the fluid. The rate of decomposition of HOCl is proportional to the square of the HOCl concentration. A tight seal on a preservation tank 202 housing the HOCl decreases the rate of decomposition (i.e., minimizes the release of chlorine and the introduction of oxygen).

The preservation system 200 may include a reagent tank 252 housing a sodium hydroxide solution for delivery to the preservation tank 202 for mixture with the hypochlorous acid solution being stored therein. The introduction of sodium hydroxide (or a sodium hydroxide solution) may salt out any hydrochloric acid being produced through decomposition of the hypochlorous acid (HCl+NaOH→NaCl+H2O).

The preservation system 200 may be configured, as described above, to titrate sodium hydroxide into the preservation tank 203 at a rate for preserving the pH of the solution therein, such as within a range of 5.95-6.05 pH, in order to minimize the decomposition of the hypochlorous solution. Further, the preservation system may maintain the temperature of the hypochlorous within a specified range, such as within 33° F.-42° F. Experimental data suggests that the hypochlorous solution will remain well preserved for at least 6 months with less than a 15% decomposition of HOCl by adapting the methods and systems described in this Example 4.

Dry Fog Delivery System.

According to further embodiments of the disclosed system 1, once a solution 10 is produced by the production system 100 and/or preserved by the preservation system 200, a dry fog delivery system 300 and methods of use may deliver the solution 10 within an environment 3. In some embodiments, the environment 3 is closed. The dry fog delivery system 300 may produce droplets 302 of the solution 10 within certain size ranges 304. In some embodiments the size ranges 304 of the droplets 302 produced are under ten microns, between four and ten microns, or under fifteen microns. Dry fog delivery systems 300 disclosed herein may be used to sanitize or disinfect the surfaces 5 or air within an environment 3 in a manner that doesn't moisten the surfaces 5 exposed to the droplets 302.

The dry fog delivery system 300 may include a fog tank 310 for housing the solution 10. In some embodiments of the system 1, the fog tank 310 of the fog delivery system 300 is the same solution tank 180 (or another solution tank 181) of the production system 100 and/or the preservation tank 202 (or preservation solution tank 260) of the preservation system 200, and may be engaged one or more of the systems 100, 200, 300 and incorporated for use in one or more of the systems 100, 200, 300 accordingly. In other embodiments, the solution tank 180 (or another solution tank 181) may be disengaged and sealed from the production system 100, or the preservation tank 202 (or preservation solution tank 260) may be disengaged and sealed from the preservation system 200 for transportation and engagement with the fog delivery system 300 for use as a fog tank 310 therein. In other embodiments, the solution tank 180 (or another solution tank 181) or the preservation tank 202 (or preservation solution tank 260) may be in engageable with the fog tank 310.

The fog tank 310 may include a solution reception aperture 312S for receiving the solution 10 from a solution reception hose 314S in sealed and fluidic engagement with a solution tank 180, another solution tank 181, preservation tank 202, preservation solution tank 260, a fog solution tank 350, and/or another receptacle housing the solution 10. A fog solution pump 352 may be positioned along the solution reception hose 314S or incorporated into the fog tank 310, solution tank 180, another solution tank 181, preservation tank 202, preservation solution tank 260, fog solution tank 350, and/or another receptacle housing the solution 10 for effectuating the delivery of the solution 10 through the fog tank 310. Due to instability of many solutions 10, the fog tank 310, as is more fully described above, may be configured, amended and/or manufactured for blocking ultraviolet light or sunshine, minimizing contact with environmental air, controlling the temperature and/or minimizing adverse interactions with the fog tank 310 components and/or surfaces.

The fog tank 310 may further include one or more fog generators 320 for converting the solution 10 into dry fog droplets 302. The fog delivery generator 320 may include any dry fog droplet generators known in the prior art. For example, the generator(s) 320 may include a vibrating mesh nebulizers driven by a piezo disc which pumps the solution 10 through an array of mesh apertures for generating droplets 302. In another example, the generator(s) 320 may include an ultrasonic transducer, which may be tuned to produce a fine mist of droplets 302. In some embodiments, the dry fog generator(s) 320 may produce uniformly-sized droplets 302. In other embodiments, the dry fog generator(s) 320 include specialized spray nozzles that emit a spectrum of particle sizes within the droplet size range 304.

The high surface tension of the droplets 302 may minimize the ability for water to condense on the surface of the droplets 302, thereby permitting water vapor to be more precisely controlled. Dry fog systems 300 and their resulting droplets 302 are designed to only agglomerate to airborne dust, not wet the surfaces 5 located in the environment 3 where the droplets 302 are being dispersed. For example, for a solution 10 being hypochlorous acid, the dry fog delivery system 300 may produce droplets 302 with a size range 304 under ten microns in diameter for minimizing water condensation on the droplets 302.

In the prior art, when many solutions 10, such as those containing a constituent (e.g., hypochlorous acid) mixed with water, are nebulized, the droplets 302 generated tend to shrink in size at a rate as the percentage relative humidity in the environment 3 decreases (forming an inverted, negatively sloped curve when droplet size is on the y-axis and relative humidity is on the x-axis). The shrinkage of size of the droplet 302 when the relative humidity is low is due to evaporation of water in the droplet 302, the main constituent of many solutions 10. The decreasing size of the droplet 302 changes the chemistry within each droplet 302. The concentration of other, non-water constituents (e.g., hypochlorous acid) increases as the droplet size decreases.

In the example of hypochlorous acid specifically, this increase in the concentration of the hypochlorous acid decreases the pH. Once the pH level of the droplet 302 crosses below the four pH threshold, for example, chlorine gas begins to form at a significant rate (as is evidenced by the free chlorine pH dissociation curve) and is released from the droplet 302, creating a hazardous environment 3 and the hypochlorous droplets 302 having less effectiveness, since the chlorine gas is heavier than air and tend to sink to the lowest point in a given environment 3, particularly when the environment is closed 3. As is depicted in the free chlorine pH dissociation curve, the optimal pH for a hypochlorous acid solution (from a fluid degradation and microbicidal perspective) is around 6 pH, with production of chlorine gas increasing as the pH drops and the concentration of hypochlorite (a less effective oxidant) increasing as the pH rises.

Figure 6:
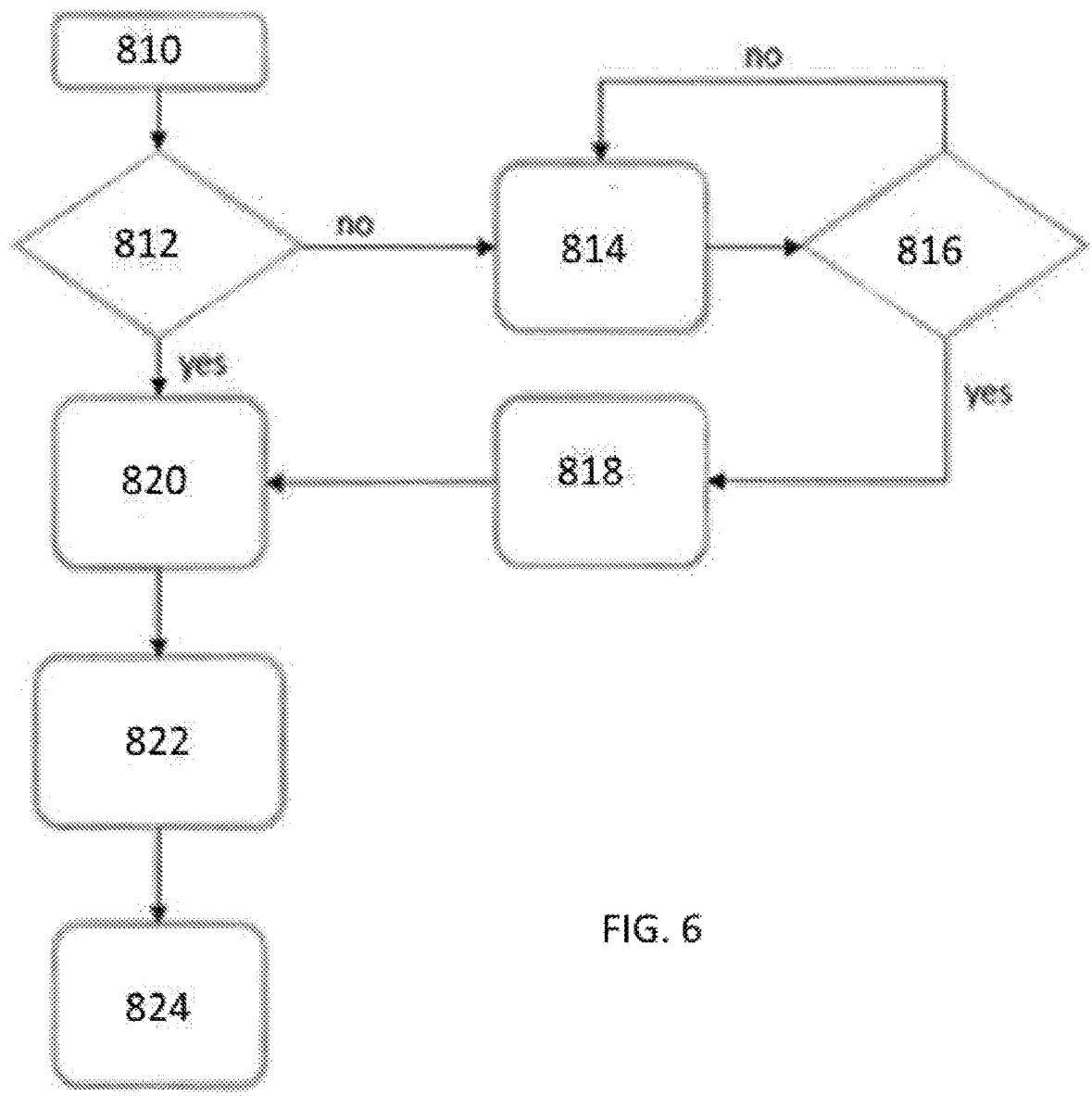
Figure 7:
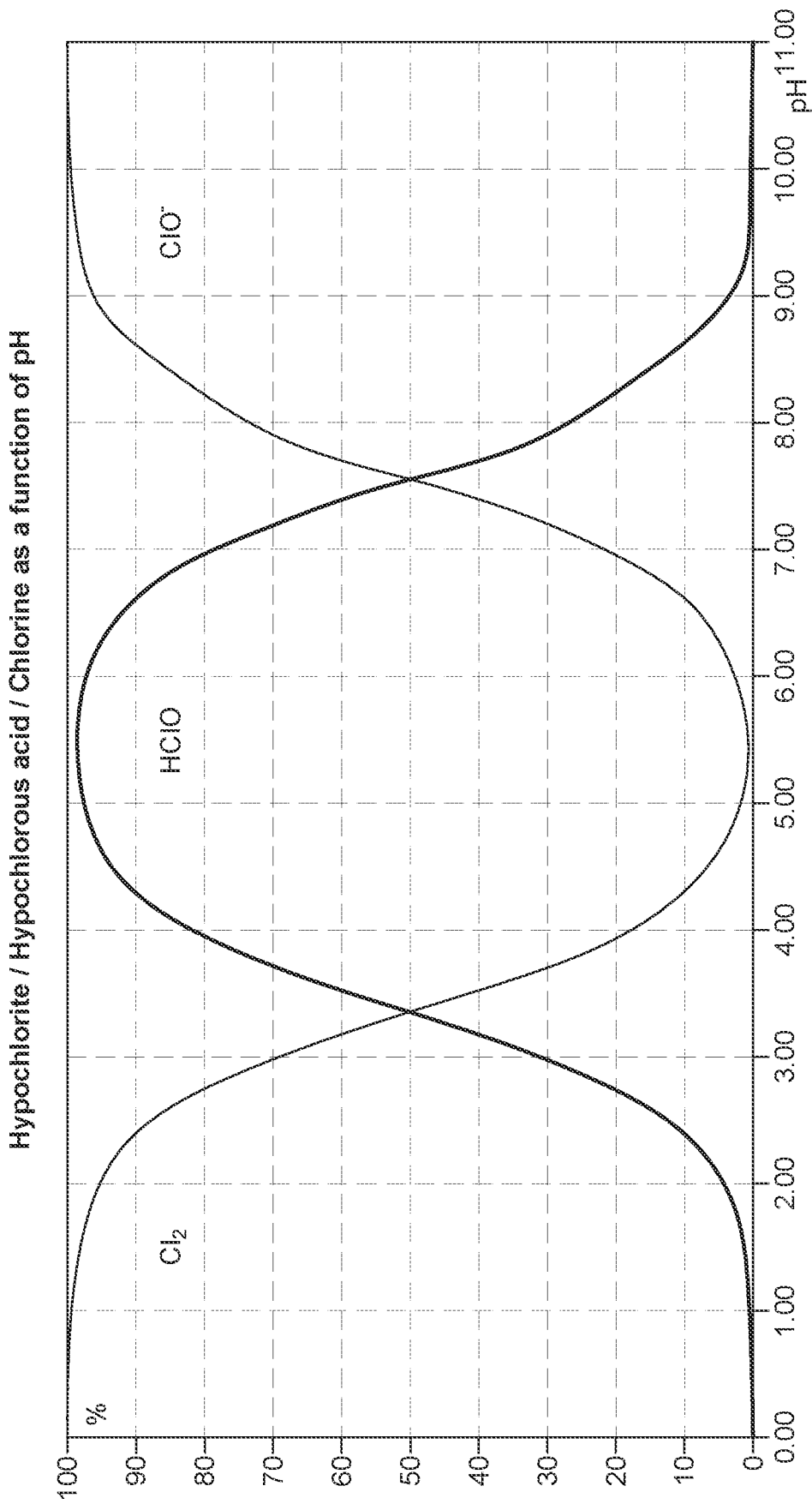
Figure 9:
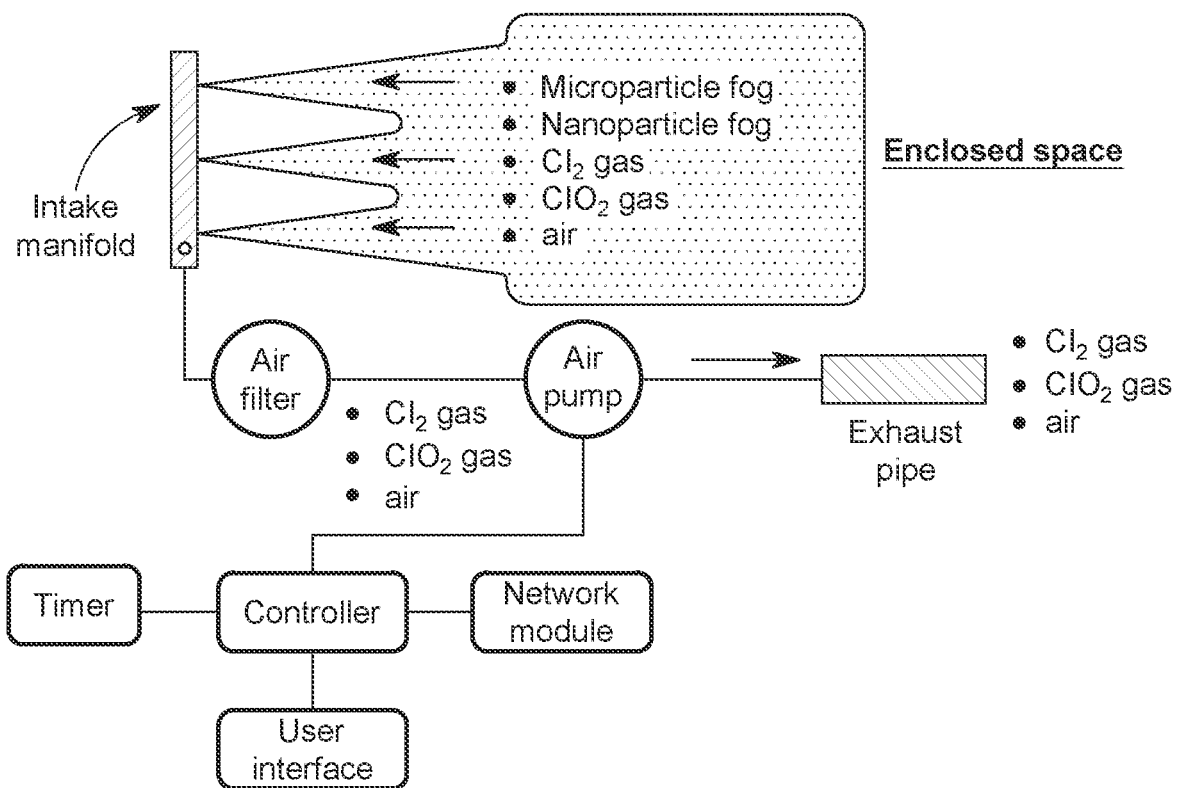
Figure 10:
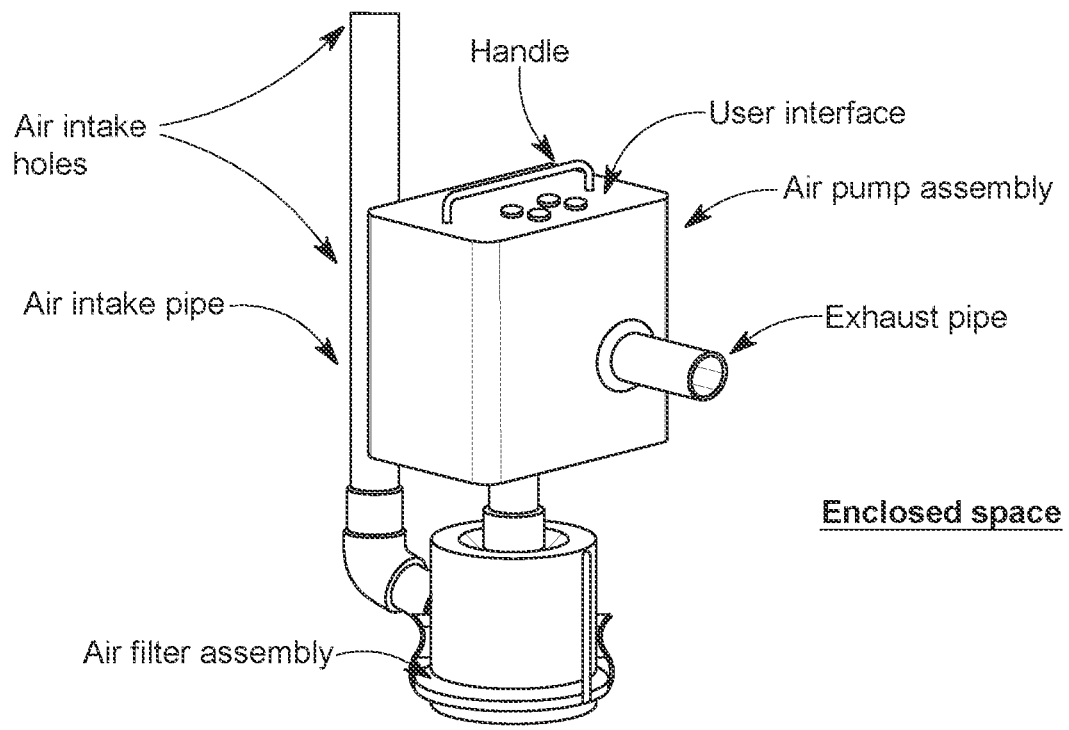
Figure 11:
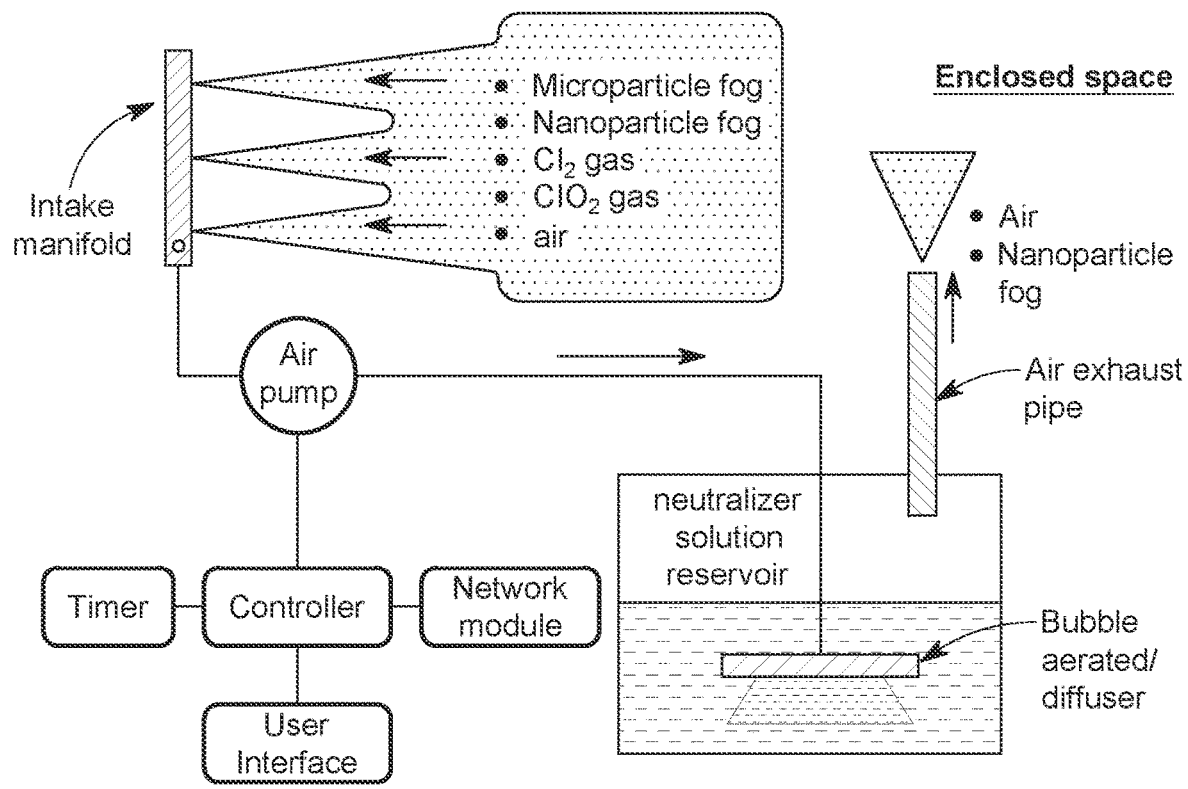
Figure 12:
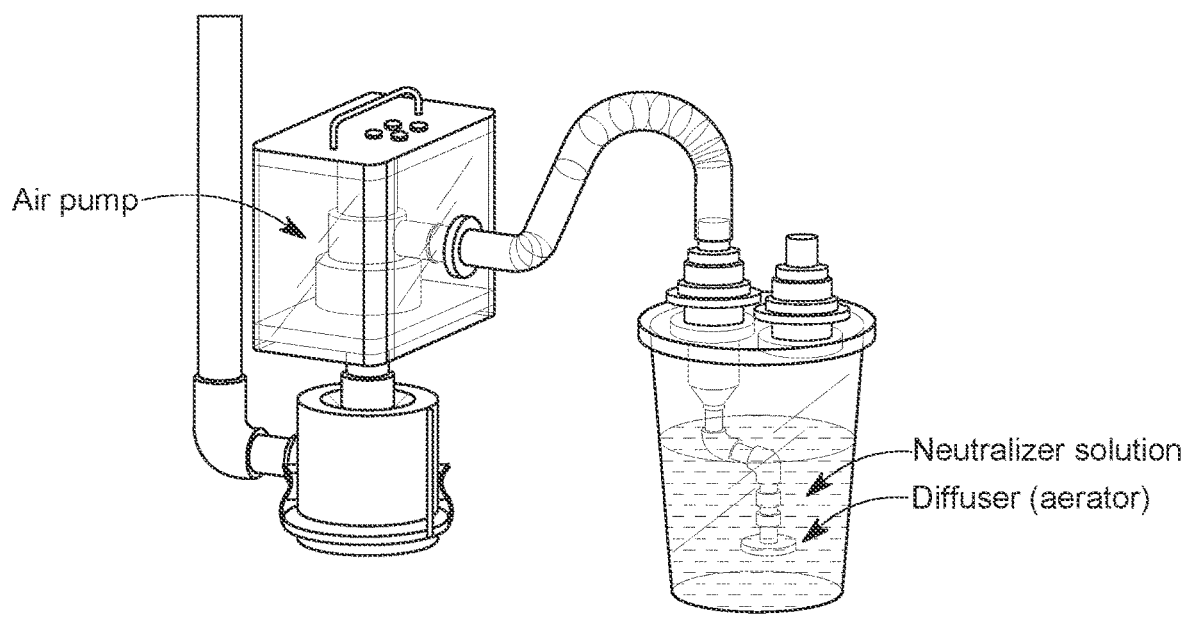

In FIG. 6, the system 1 may start 810, then determine if the relative humidity is greater than or equal to 80% 812. If yes, the start water dry fog delivery 814, then determine if the relative humidity is greater than or equal to 80% 816. If yes, then stop water dry fog delivery 818 and start HOCl dry fog delivery 820, then wait for a period of time 822, then stop HOCl dry fog delivery.

The presently disclosed dry fog delivery system 300 offers a solution to the issues exampled above of the prior art. Experimentation has shown that the size shrinking rate of droplets 302 having solutions 10 constituting water is minimal when the relative humidity in an environment 3 crosses beyond the 80% threshold. Droplets 302 dispensed into the environment 3 when the relative humidity is at or above 80% remain roughly the same size. By increasing and maintaining the relative humidity in an environment 3 at or above 80%, dry fog dispersion of droplets 302 may be much more effective since the chemistry inside the droplet 302 remains stable.

In some embodiments of the presently disclosed system 1, the dry fog delivery system 300 may incorporate various sensors 160, 210. To measure when the solution 10 or environment 3 has a delivery condition 340, the delivery system 300, fog tank 310, fog solution tank 350, water tank 336 may include one or more sensors 160, 210 for sensing a delivery condition 340 of the solution 10, the environment 3, the delivery system 300 and/or the delivery tank 31. The one or more sensors 160, 210 may be positioned within or on the delivery system 300 and/or delivery tank 310 or may insertable therewithin. One or more sensors 160, 210 may be positioned with the environment 3. For example, two or more relative humidity sensors 160R may be included in various positions throughout a closed environment 3 for measuring the relative humidity within the environment 3. One or more of the sensors 160, 210 may be housed together. Additional sensors 160, 210 and their uses are described further herein and may be applied to the delivery system 300.

In some embodiments, the delivery system 300 may include a pH sensor 160P, a temperature sensor 220T and/or a fluid level sensor 160F for sensing various delivery conditions 340 (e.g., the fluid level, temperature and/or pH of the fog tank 310).

To measure when the environment 3, whether open or closed, meets a delivery condition 340 being a relative humidity range (e.g., above 80%), the dry fog delivery system 300 may include one or more relative humidity sensors 160R for sensing the relative humidity of the environment 3.

According to some embodiments, the delivery system 300 further includes a humidifier 330 for dispersing water or a water-containing solution 332 into the environment 3 for increasing and maintaining a high relative humidity. The humidifier 330 may be sealingly engaged with a humidifier hose 334 for delivering the water solution 332 from the water solution tank 336. A humidifier pump and/or valve 338 may be positioned along the humidifier hose 334 or incorporated into the water tank 336 or humidifier 330 for effectuating the delivery of the water solution 332 through the humidifier hose 334.

In other embodiments, the fog tank 310 may be configured for dispersing both the solution 10 and the water solution 332. The fog tank 310 may further include a water reception aperture 312W for receiving the water solution 332 from a water tank hose 314W in sealed and fluidic engagement with a water tank 336. The water pump 338 may be positioned along the water tank hose 314W or incorporated into the water tank 336 or fog tank 310 for effectuating the delivery of the water solution 332 through the fog tank 310 to the generator 320.

In one embodiment of the dry fog system 300, a method of maintaining a delivery condition 340 for the system 1, environment 3, solution 10, delivery system 300 and/or fog tank 310 is provided. The delivery condition 340 may include a value or a specific range of values for one or more specific conditions (e.g., temperature, pH, humidity, time, concentration, fluid level, etc.). One or more of the sensors 160, 210 may be employed to measure various conditions 2 of the system 1, environment 3, solution 10, preservation system 200 and/or preservation tank 202. An actual delivery condition 342 may be directly measured or may be calculated or determined by the dry fog control unit 360 using one or more of the other conditions 2. If the actual delivery condition 340 matches, or falls within, the delivery condition 340, the delivery system 300 may remain unchanged for a waiting period 274. If the actual delivery condition 342 does not match, or falls without, the delivery condition 340, one or more components of the delivery system 300 may be changed through an action 4.

According to some embodiments, the dry fog delivery system 300 includes a dry fog control unit 360. The dry fog control unit 360 may be in wireless and/or electrical communication with various sensors 160, 210, the fog delivery generator 320, the humidifier 330, the water pump 338, and/or the fog solution pump 338. In a dry fog system 300 including a humidifier 330 or dry fog generator 320 in fluidic engagement with a water tank 336 for dispersing the water solution 332 into an environment 3, the dry fog control unit 360 may be in wireless and/or electrical communication with a relative humidity sensor 160R and the humidifier 330 and/or dry fog generator 320.

According to at least one method, the dry fog control unit 360 determines, via one or more relative humidity sensors 160R, whether the actual delivery condition 342 being relative humidity of the environment 3 falls within a delivery condition 340 (e.g., greater than 80% relative humidity). If the actual condition 342 falls within the delivery condition 340 then a waiting period 274 may pass before another determination. If the actual condition falls without the delivery condition 340, then the dry fog control unit 360 may activate the humidifier 330 or dry fog generator 320 (and/or water pump 338) for dispersing the water solution 332 into the environment 3 for a specified period of time, thereby attempting to increase the relative humidity of the environment 3 to within the delivery condition 340. These methods steps may be repeated.

According to at least another method, the dry fog control unit 360 first determines, via one or more relative humidity sensors 160R, whether the actual delivery condition 342 being relative humidity of the environment 3 falls within a delivery condition 340 (e.g., greater than 80% relative humidity). If the actual condition 342 falls within the delivery condition 340 then the control unit 360 activates the dry fog generator 320 (and/or fog solution pump 352) for dispersing the solution 10 into the environment 3 for a specified period of time. Once the dispersal of the solution 10 is ceased, another actual condition 342 determination is made by the dry fog control unit 360. If, again, the actual condition 342 falls within the delivery condition 340 then the control unit 360, again, activates the dry fog generator 320 for a specified period of time. If, however, the actual condition 342 falls without the delivery condition 340, then the dry fog control unit 360 may activate the humidifier 330 or dry fog generator 320 for dispersing the water solution 332 into the environment 3 for a specified period of time, thereby attempting to increase the relative humidity of the environment 3 to within the delivery condition 340. Once the water solution 332 dispersal ceases, another actual delivery condition 342 is made. If, again, the actual condition 342 falls without the delivery condition 340, the water solution 332 dispersal repeats. If, however, the actual condition 342 falls within the delivery condition 340, the solution 10 dispersal is effectuated by the dry fog control unit 360.

The methods described in the preceding paragraph ensure that the dispersal of the water solution 332 may not run simultaneously with the solution 10 dispersal, thereby minimizing the undesired reaction of water with the solution droplets 302 (e.g., creating chlorine gas when the solution 10 is hypochlorous acid).

In some embodiments, a plurality of reservoir tanks 380 corresponding to one or more of the reservoirs 374 may be included in the dry fog delivery system 300 for storing the fluids for delivery to the corresponding reservoirs 374 via hoses, pumps and/or apertures. Sensors 160, 210 may be incorporated within or proximal these reservoir components for sensing various conditions (e.g., fluid levels, temperature, pH, etc.). In other embodiments, the reservoir tanks 380 may also incorporate the systems and methods of the preservation system 200 by doubling as preservation tanks 202.

The mesh nebulizer modules 386 may take many forms, like the nebulizers of the generators 320, and, like the generators 320, may be made from a chemical resistance coating or materials with chemically resistant properties such as stainless steel, titanium polyamide, gold, palladium or other chemical resistant materials, metals or plastics. The nebulizer modules 386 may beultrasonic transducers.

Multiple nebulizer modules 386 may be wired in parallel if driven by the same driver circuit. The piezo driver may have a current sense signal capable of being converted to a digital value via an analog to digital converter circuit. The master controller 9, the dry fog control unit 360 or other control units described herein may determine if all the mesh nebulizer modules are working properly throughout the application of the coating. If it is determined that one or all of the mesh nebulizer modules are not working, the master controller 9, the dry fog control unit 360 or other control units described herein may flag an error. It may notify the operator through the user interface or the operator via text through the network communication system. The processor may control the piezo driver via anon/off signal. The processor may determine the condition of the nebulizer by reading the current sense signal via the analog to digital converter circuit.

During operation, the dry fog may be dispersed and the air filtration may operate simultaneously, in alternating rotation, or subsequently. Timing schedules may be determined and/or used to control operation. Using sensed actual conditions 22, information and determined data, the application of the dry fog and filtration may be controlled.

Byproduct Collection and Neutralization.

According to further embodiments of the disclosed system 1, once a solution 10 is dispersed via droplets 302 by the dry fog delivery system 300 within an environment 3, the solution 10 may interact with the environment 3 and/or decompose over time to create fog byproducts 602 (e.g., chlorine gas or chlorine dioxide gas). The system 1 may further include a collection system 400 for collecting and/or neutralizing the solution 10, byproducts 602 and/or air 6 of the environment 3. The environment 3 may be closed or sealed.

Some regulatory agencies, such as the U.S. Environmental Protection Agency, require the registration of a some solutions 10 if it is to be produced and distributed from a central location. The tests required for the registration of a biocide for fogging applications, for example, are more elaborate and pricier than for surface cleaning applications. Therefore, it may be advantageous to contend that aerosols, harmful or otherwise, remain in the sanitized or disinfected space after the application of fog and the fog's removal, as is disclosed by the systems and methods described herein.

According to one embodiment, the collection system 400 may include a gas collection system 402 for collecting and neutralizing gas and/or microparticles. The collection system 400 may include a particle collection system 404 for collecting and neutralizing nanoparticles and microparticles. A collection control unit 440 may be utilized by the collection system 400 for controlling the particle and gas collection systems 404, 402, accepting sensed information from the sensors 160, 210, and/or making determinations based on the sensed information.

The particle collection system 404 may include an particle intake manifold 410 containing any number of intake apertures 412 for collecting air 6 from the environment 3. The air 6 may include droplets 302, solution 10, fog byproducts 602 and/or other constituents of the environment 3. The intake manifold 410 may be in fluidic communication with an air filter assembly 414 including one or more air filters 416 or may contain one or more air filters 416 therein. The intake manifold 410 and/or air filter assembly 414 may be in fluidic communication with an air pump assembly 420 including an air pump 422 or may contain an air pump 422 therein. In some embodiments, the air filter assembly 414 may also include an air pump 422. In such embodiments, the particle collection system 404 may collect microparticles, nanoparticles and gases and exhaust the gas, through an exhaust pipe 424 engaged with the intake manifold 410 or air pump assembly 420 or air filter assembly 414.

The gas collection system 402 may include an gas intake manifold 430 containing any number of intake apertures 432 for collecting air 6 from the environment 3. The air 6 may include dry fog droplets 302, solution 10, fog byproducts 602 and/or other constituents of the environment 3. The intake manifold 430 may be in fluidic communication with an gas air pump assembly 440 including an air pump 442 or the manifold 430 may contain an gas air pump 442 therein. The gas collection system 402 may also include a neutralization tank 450, housing a gas neutralizing reagents 458, and in fluidic communication with the manifold 430 and/or the air pump assembly 440 via a gas collection hose 452 extending through a gas collection aperture 454 of the neutralization tank 450. The gas collection hose 452 may include a gas collection diffuser 454 thereon for aerating the collected air 6 and neutralizing certain gases therein, such as chlorine gas or chlorine dioxide. The neutralization tank 450 may include an exhaust pipe or aperture 456 for exhausting the remaining air 6 therefrom, including any nanoparticles contained therein that may not have dissolved in the gas neutralizing reagents 458. In such embodiments, the particle collection system 404 may collect microparticle fog, nanoparticle fog and gases and exhaust gas, through an exhaust pipe 424 engaged with the intake manifold 410 or air pump assembly 420 or air filter assembly 414.

In alternative embodiments, the gas intake manifold 430 may be in fluidic communication with an air filter assembly 434 including one or more air filters 436 or may contain one or more air filters 436 therein so that the gas collection system 402 may also collect and neutralize nanoparticles. In such an embodiment, the air filter assembly 434 may be in fluidic communication with an air pump assembly 440.

The air filters 416, 436 may by a HEPA filter.

The operation of the collection system 400 may be concurrent or sequential, and/or may be in coordination with control units for matching conditions 2. In some embodiments, the operation of the gas collection system 402 and/or particle collection system 404 may be solely based on time, with each or both operating for certain lengths of time and resting for other lengths of time.

In some embodiments the dry fog system 300 may be run in coordination with the collection system 400. For example, the dry fog system 300 may be initiated and ran for a set time period, after which the collection system(s) 400 may be initiated and ran for another set time period. Once the first cycle of fogging, neutralizing and collecting is completed, the environment 3 may be disinfected or sanitized for further removing concentrations of nanoparticles, microparticles, chlorine gas and chlorine dioxide gas, so that these concentrations do not exceed unsafe levels. In some embodiments, the collector systems 400 may not run in unison but may have staggered and/or alternating time periods, with concurrent and/or sequential runs.

Feedback-based operations rely on feedback algorithms for running the dry fog system 300 and/or the collection system(s) 400. For example, the dry fog system 300 may run for a period regulated by a feedback algorithm tuned to achieve a specified level of disinfection or sanitation. The algorithm may consider the type of microbes being targeted, the specified microbial load reduction to be achieved, the concentration of droplets 302 in the environment 3 and dwell period, the relative humidity over the disinfection or sanitation period, and other information. The dry fog system 300 and/or collection system(s) 400 may run concurrently to reduce chlorine gas and chlorine dioxide gas levels in the environment 3 during the dry fogging. In this mode, the operator may be notified that the disinfection or sanitation cycle is complete via a wireless user interface, alarm system or through a visual indicator.

The collection system(s) 400 may be capable of removing microparticle fog, neutralizing chlorine gas, and/or neutralizing chlorine dioxide gas. In some embodiments, nanoparticles may be encapsulated inside small, aerated bubbles, instead of being dissolved into the neutralization reagents 458. In such cases, these nanoparticles may escape back into the atmosphere. An inline filter, may be provided for capturing these nanoparticles and removing them. In other embodiments, the filter assembly may remain empty. The nanoparticle fog may be generated as a result of the evaporation that occurs when of microparticle fog that is generated in low RH conditions(<80% RH).

An additional tank 470 may be daisy-chained to the first neutralization tank 450 to prevent the splashing and exit of neutralization reagents 458 into the environment 3 during operation.

To prevent the release of too much of too much gas into the environment, a control unit may activate the pump 422, 442 intermittently.

In some embodiments, the collection system(s) 400 may be provided for removing micron and submicron sized aerosolized particles from the environment 3, which may be hazardous if inhaled. The fog collection systems may utilize a HEPA or other type of air filter and an inline air pump. When the fog collection system is in operation, it may pull air from inside the chamber into the air filter and returns clean air. The air pump may run for a duration determined according to that particle count inside the chamber for preventing hazardous conditions. The machine controller and/or sensor system may monitor the use of the fog collection system, which may include sensing the cycle count, particle accumulation and/or collection, determining the need for air filter replacement, or locking the system down when hazardous conditions are present.

EXAMPLE 5. The neutralizer solution (sodium thiosulfate, sodium hydroxide and water), when combined with HOCl may undergo multiple reactions with free and combined chlorine, depending on the solution pH. The amount of sodium thiosulfate required for neutralization may vary with solution pH. Any hydrochloric acid produced may be salted out by the sodium hydroxide (HCl+NaOH→NaCl+H2O).

$$Na2S2O3+4HOCl+H2O \rightarrow 2Na2SO4+4HCl$$

$$Na2S2O3+HOCl \rightarrow Na2SO4+S+HCl$$

$$2Na2S2O3+HOCl \rightarrow Na2S4O6+NaCl+NaOH$$

Chlorine gas in the neutralizer solution produces hydrochloric acid (HOCl). HOCl may be neutralized, as shown above. As stated, any hydrochloric acid produced may be salted out by the sodium hydroxide.

$$Cl2+H2O \rightarrow HCl+HOCl$$

Chlorine dioxide gas in the neutralizer solution produces sodium bisulfate and hydrochloric acid. As stated above, any hydrochloric acid produced will be salted out by the sodium hydroxide.

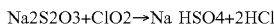

$$Na_2S_2O_3 + ClO_2 \rightarrow Na\ HSO_4 + 2HCl$$

General Features.

The production system 100 and/or the preservation system 200 may be closed systems and may be in sealed engagement with each other. Further, the production system 100 and/or the preservation system 200 may be in sealed engagement with the dry fog production system 300.

Any of the tanks disclosed herein (102, 106, 130, 140, 180, 190, 202, 234, 252, 260, 310, 336, 350, 380, 412) may be insulated, temperature-controlled and/or opaque using methods and systems described herein, or in the prior art. Any tanks may be comprised of or coated with any number of materials, including, but not limited to any combination or layered combination of glass, PVDF, Teflon (PTFE), Viton, Nitrile, Kalrez, or Acrylic. Any tanks may have a number of properties for blocking ultraviolet light or sunshine (e.g., including opaque, light reflecting materials), minimizing contact with environmental air, controlling the temperature and minimizing adverse interactions with any components or interior surface of the tank. Any tank may include water-tight and/or air-tight seals on their apertures to minimize interactions of their content with the environment 3. Whereas most tanks are closed within a system or sealed, some tanks, like the production tank 130, may include an open side for interacting with the environment 3. Some other tanks may permit gaseous exchange with the environment 3. Some tanks may include an insulating layer thereabout for further ensuring a stable or controllable internal temperature. Tanks may come in any number of shapes, and may be mobile or affixed with mobile features, such as wheels or handles. The tanks may include an aperture and/or valve on the nadir of the tank for easy emptying and/or cleaning.

The reservoirs 374 may be comprised of the same materials described above in relation to tanks. Alternatively, the reservoirs 374 may be comprised of, or contain a layer of, one or more of the following materials: plastic, rubber, HDPE, LDPE, UHMWPE, PTFE, acrylic, polypropylene, Viton, PVDF, CPVC, Nitrile, EDPM, nitrile, neoprene, polyurethane, and silicone. The reservoirs 374, like tanks, may be resistant to certain chemical and/or contain gaskets or other designed components (e.g., check valves or membranes) to prevent leaks and form a watertight seal. Some designs may permit gaseous but not fluidic exchange.

Any of the valves disclosed herein 116, 174, 188 may include a combination of valves, tees, pumps, and/or couplings, and may be manually or automatically operated.

Any of the pumps disclosed herein 176, 186, 240, 242, 244, 338, 352, 406 may include a combination of pumps, valves and/or couplings, and may be manually or automatically operated.

The tanks may be interconnected using a plurality of hoses, valves and pumps to form closed systems. These interconnections may further involve apertures, regulators, sensors and/or controllers.

Automatic operation may occur through one or more controllers known in the prior art and/or described herein. The system 1 may include a master controller 9 in wireless or electronic communication with any combination of controllers disclosed herein (220, 360, 440). Any of the controllers, which further includes the master controller 9 and controllers of the prior art, may include or being in communication with one or more sensors 160, 210 for receiving sensed conditions. The controllers may include programmable logic circuits, memory and/or software to monitor and make determinations. Any of the controllers may be a standalone or web-based system. Each of the components of the system 1 may communicate electronically or wirelessly, amongst each other or through or in conjunction with one or more of the controllers. The controllers may be web-based and each system component may be in communication with the controller via wireless or wired internet connection(s). Internet connectivity may be facilitated by a Wi-Fi network with internet connectivity, an ethernet connection with internet connectivity or a wireless cellular data network connection. Additionally, the system architecture may not require a controller module or a relative humidity sensor, particle counter, chlorine gas sensor, or chlorine dioxide sensor if the timer-based system is implemented.

Any of the sensors 160, 210 may be equipped to measure any number of conditions known in the prior art to be sensed (e.g., concentration, duration, temperature, pressure, flow rate, humidity, fill level, back flow, malfunctions, etc.). If any sensor or controller detects or determines a malfunction, an auto-shut-off and/or neutralization method may be initiated.

For each sensor or controller, a display panel, operational controls and/or wireless communication features for operation may be provided. The network communication system may be employ any signal transfer technology of the art, including Wi-Fi or cellular, as depicted in the top and bottom figures respectively below. The network communication system may, among enabling other functions, permit remote identification of machine issues for troubleshooting, generate field service work orders, collect and store information about the machine use.

The user interface of the machine may include an indicator tower, a screen, buttons and/or messaging communications. The user interface may indicate, display and/or provide control functionality. Machine modes, errors of the machine as a whole or components thereof, network connectivity, sensed or determined data, or status of the machine or components may be indicated or displayed. The network communication system may permit the user interface(s) to be housed on or proximal to the machine or sealed chamber, remotely positioned, and/or mobile.

What is claimed is:

1. A system for dispersing a solution into an environment, comprising:

a preservation tank having an exterior for blocking ultraviolet light, wherein the preservation tank is configured to store a solution therewithin;

a temperature sensor configured to measure a temperature of the solution;

a coil positioned within the preservation tank for receiving a refrigerant therethrough;

a coil pump in communication with the temperature sensor and configured for pumping the refrigerant through the coil when the temperature sensor measures the temperature to exceed a threshold temperature;

a pH sensor configured to measure a pH of the solution;

a pH aperture defined by the preservation tank for receiving a reagent therethrough;

a reagent pump in communication with the pH sensor and configured for pumping the reagent through the pH aperture into the preservation tank when the pH sensor measures the pH below a threshold pH;

a dispersal aperture defined by the preservation tank in fluidic communication with a fog generator, wherein the fog generator is configured to disperse the solution as droplets sized less than ten microns.

2. The system of claim 1, wherein the solution is hypochlorous acid, wherein the threshold temperature is 42 degrees Fahrenheit and wherein the threshold pH is 5.95.

3. The system of claim 1, further comprising:
a humidity sensor configured to measure a relative humidity of the environment;
a water tank housing water and in fluidic communication with the fog generator;
a water pump in communication with the humidity sensor and configured for pumping the water to the fog generator for dispersal when the humidity sensor measures the relative humidity below a threshold relative humidity.

4. The system of claim 3, wherein the threshold relative humidity is 80%.

5. The system of claim 1, further comprising:
a humidity sensor configured to measure a relative humidity of the environment;
a water tank housing water and in fluidic communication with a humidifier;
a water pump in communication with the humidity sensor and configured for pumping the water to the humidifier for dispersal when the humidity sensor measures the relative humidity below a threshold relative humidity.

6. The system of claim 5, wherein the threshold relative humidity is 80%.

7. The system of claim 1, further comprising
a gas aperture defined by the preservation tank for receiving a gas therethrough;
a reagent aperture defined by the preservation tank for receiving a reagent therethrough, wherein the a mixture of the gas and the reagent creates the solution;
a gas hose extending through the gas aperture and engaging a diffuser positioned proximal a nadir of the preservation tank.

8. The system of claim 7, wherein the gas is chlorine gas, the reagent is a sodium hydroxide water solution, and the solution is hypochlorous acid.

9. The system of claim 1, further comprising:
a production tank defining:
a gas aperture for receiving a gas therethrough;
a reagent aperture for receiving a reagent therethrough, wherein a mixture of the gas and the reagent creates the solution;
a delivery aperture defined by the production tank and positioned proximal a nadir of the production tank;
a delivery pump for delivering the solution from the production tank through a delivery hose in fluidic communication with the delivery aperture to the preservation tank.

10. The system of claim 9, wherein the gas is chlorine gas, the reagent is a sodium hydroxide water solution, and the solution is hypochlorous acid.

11. The system of claim 9, further comprising a gas hose extending through the gas aperture and engaging a diffuser positioned proximal the nadir of the production tank.

12. The system of claim 1, further comprising:
an air pump in fluidic communication with an air intake and a diffuser configured for pumping air from the environment through the intake to the diffuser;
a filtration tank housing the diffuser within a reagent for neutralizing gas from the air.

13. The system of claim 12, further comprising an air filter positioned between the air intake and the diffuser for filtering particles from the air.

14. The system of claim 12, further comprising a second air pump in fluidic communication with a second air intake and a filter for pumping air from the environment through the intake and filter for filtering particles from the air.

15. The system of claim 12, wherein the environment is a sealed environment, the system further comprising a hose extending through a wall of the sealed environment, the hose being in fluidic engagement with the air pump positioned outside of the sealed environment and the air positioned within the sealed environment.

* * * * *